(12) United States Patent  (10) Patent No.: US 8,058,276 B2
Bold et al.  (45) Date of Patent: Nov. 15, 2011

(54) HETEROBICYCLIC CARBOXAMIDES AS INHIBITORS FOR KINASES

(75) Inventors: Guido Bold, Gipf-Oberfrick (CH); Andrea Vaupel, Riehen (CH); Marc Lang, Mulhouse (FR)

(73) Assignee: Novartis AG, Basel (CH)

( * ) Notice: Subject to any disclaimer, the term of this patent is extended or adjusted under 35 U.S.C. 154(b) by 389 days.

(21) Appl. No.: 12/281,715

(22) PCT Filed: Mar. 9, 2007

(86) PCT No.: PCT/EP2007/052217
§ 371 (c)(1),
(2), (4) Date: Sep. 4, 2008

(87) PCT Pub. No.: WO2008/009487
PCT Pub. Date: Jan. 24, 2008

(65) Prior Publication Data
US 2009/0030009 A1  Jan. 29, 2009

(30) Foreign Application Priority Data

Mar. 10, 2006 (GB) .................................. 0604937.3

(51) Int. Cl.
*C07D 413/12* (2006.01)
*C07D 417/12* (2006.01)
*A61K 31/41* (2006.01)
(52) U.S. Cl. ................... 514/252.14; 514/269; 544/295; 544/319
(58) Field of Classification Search ................ 544/295, 544/319; 514/252.14, 269
See application file for complete search history.

(56) References Cited

FOREIGN PATENT DOCUMENTS

| WO | 2005/012298 A | 2/2005 |
|----|---------------|--------|
| WO | 2006/059234 A | 6/2006 |

OTHER PUBLICATIONS

Simone, Oncology: Introduction, 20th Edition, vol. 1, pp. 1004-1010, 1996.*
Traxler, Protein tyrosine kinase inhibitors in cancer treatment, Exp. Opin. Ther. Patents, 7(6), pp. 571-588, 1997.*
Search Report Prepared for PCT/EP07/052217 on Oct. 17, 2007 by the European Patent Office.

* cited by examiner

*Primary Examiner* — Deepak Rao
(74) *Attorney, Agent, or Firm* — John B. Alexander

(57) ABSTRACT

The invention relates to novel organic compounds of formula (I) and their use in the treatment of the animal or human body, to pharmaceutical compositions comprising a compound of formula (I) and to the use of a compound of formula (I) for the preparation of pharmaceutical compositions for use in the treatment of protein kinase dependent diseases, especially of proliferative diseases, such as in particular tumour diseases.

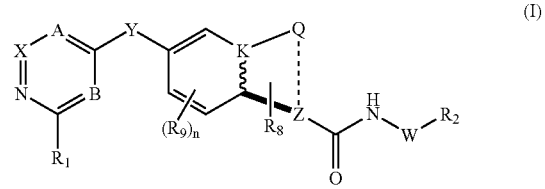

5 Claims, No Drawings

HETEROBICYCLIC CARBOXAMIDES AS INHIBITORS FOR KINASES

The invention relates to bicyclic heterocyclyl compounds substituted at both rings of formula I and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in particular tumour diseases.

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive wild-type or mutated PK activity has been observed in many disease states including benign and malignant proliferative disorders. In many cases, it has been possible to treat diseases, such as proliferative disorders, by making use of PK inhibitors.

In view of the large number of protein kinases and the multitude of proliferative and other PK-related diseases, there is an ever-existing need to provide compounds that are useful as PK inhibitors and thus in the treatment of these PK related diseases.

It has now been found that the compounds of formula I show inhibition of a number of protein kinases. The compounds of formula I, described below in more detail, especially show inhibition of one or more of the following protein kinases: EphB4, c-Abl, Bcr-Abl, c-Kit, Raf kinases such as especially B-Raf, the rearranged during transfection (RET) proto-oncogene, Platelet-derived Growth Factor Receptors (PDGF-Rs), Lck, Hck and most especially the Vascular Endothelial Growth Factor Receptors (VEGF-Rs) such as in particular VEGF-R2. The compounds of formula I further also inhibit mutants of said kinases. In view of these activities, the compounds of formula I can be used for the treatment of diseases related to especially aberrant or excessive activity of such types of kinases, especially those mentioned. Structurally related compounds have been described in WO2006/059234

The invention especially relates to compounds of the formula I,

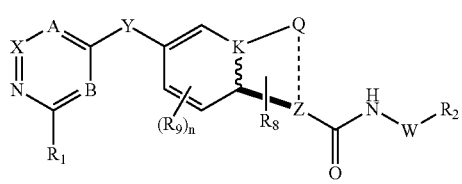

wherein
$R_1$ is H; halo; —$C_0$-$C_7$—O—$R_3$; —$NR_4R_5$;
$R_2$ is substituted aryl;
$R_3$ is H, lower alkyl or phenyl lower alkyl;
$R_4$ and $R_5$ are independently selected from the group consisting of H; unsubstituted or substituted lower alkyl; lower alkoxy-carbonyl and amino;
A, B and X are independently selected from C($R_7$) or N, with the proviso that not more than one of A, B and X is N;
$R_7$ is selected from the group consisting of H, halo and unsubstituted or substituted lower alkyl;
$R_8$ is hydrogen or lower alkyl;
$R_9$ is a substituent;
n is 0, 1, 2 or 3;
Y is O;
Z is C;
W is absent;
K is N or C, and
either
 a), if K is C,
  the bond indicated by the waved line ( ~~~ ) is a double bond,
  Q is selected from
   O—N
   S—N
   O—CH and
   S—CH
  where in each case the left O or S atom is bound by the bond shown in formula I to K, the right N or carbon atom (of CH) to C via the bond indicated by the broken line ( ------ ) in formula I, with the proviso that said bond indicated by the broken line is a double bond to C;
  and the bond represented in bold ( ▬ ) is a single bond;
or
 b), if K is N, the bond indicated by the waved line is a single bond,
 Q is

where the left N atom is bound by the bond shown in formula I to K, the right carbon atom (of CH) to C via the bond indicated by the broken line in formula I, with the proviso that said bond indicated by the broken line is a single bond to C;
 and the bond represented in bold is a double bond;
or a tautomer thereof, and/or a (preferably pharmaceutically acceptable) salt thereof.

The present invention also relates to a method of treating a kinase dependent and/or proliferative disease comprising administering a compound of the formula I to a warm-blooded animal, especially a human, and the use of a compound of the formula I, especially for treating a kinase dependent disease or disorder. The present invention also relates to pharmaceutical preparations comprising a compound of the formula I, especially for the treatment of a kinase dependent disease or disorder, a process for the manufacture of a compound of the formula I, and novel starting materials and intermediates for their manufacture. The present invention also relates to the use of a compound of formula I in the manufacture of a pharmaceutical preparation for the treatment of a kinase dependent disease.

The general terms used hereinbefore and hereinafter preferably have, within this disclosure, the following meanings, unless otherwise indicated (where preferred embodiments can be defined by replacing one or more up to all general expressions or symbols with (a) more specific or more preferred definition(s) given herein):

The term "lower" defines a moiety with up to and including maximally 7, especially up to and including maximally 4, carbon atoms, said moiety being branched or straight-chained. Lower alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

The term "$C_0$-$C_7$—" is as defined above for "lower" with the difference that in case of "$C_0$—" no carbon atom is present (that is, the moiety bound to $C_0$ is directly bound to the rest of the molecule).

Substituted lower alkyl or a substituted lower alkyl moiety is a lower alkyl radical/moiety substituted by one or more, preferably one, substituents selected independently from e.g. halo, morpholinyl-lower alkyl, piperazinyl-lower alkyl, lower alkyl-piperazinyl-lower alkyl, $C_3$-$C_8$-cycloalkylpiperazinyl, piperidinyl-lower alkyl, N-lower alkyl-piperidinyl-lower alkyl, piperidinyliden-lower alkyl or N-lower alkyl-piperidinylidene-lower alkyl, such as 1-methylpiperidin-4-ylidenemethyl, 9-loweralkyl-3,9-diaza-bicyclo[3.3.1]non-3-yl-methyl, amino, N-lower alkyl-amino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halo, or unsubstituted or substituted heterocyclyl.

Mono- or di-substituted amino (=N-mono- or N,N-di-substituted amino) (also in mono- or disubstituted aminocarbonyl or other moieties where mentioned) is amino substituted by one or two radicals selected independently of one another from e.g. substituted and especially unsubstituted lower alkyl.

Halo(geno) is preferably iodo, bromo, chloro or fluoro, especially fluoro, chloro or bromo. Substituted $C_3$-$C_8$-cycloalkyl is especially cyclopropyl or cyclohexyl and is preferably substituted as described for substituted aryl. Unsubstituted $C_3$-$C_8$-cycloalkyl is a corresponding moiety without substituent.

Substituted aryl is preferably an aromatic radical with 4 to 8 carbon atoms, especially phenyl, wherein said radical is substituted by one or more, preferably by one or two, radicals such as e.g. unsubstituted or substituted lower alkyl, such as halo-lower alkyl, morpholinyl-lower alkyl, piperazinyl-lower alkyl, lower alkyl-piperazinyl-lower alkyl, $C_3$-$C_8$-cycloalkylpiperazinyl, piperidinyl-lower alkyl, N-lower alkyl-piperidinyl-lower alkyl, piperidinyliden-lower alkyl or N-lower alkyl-piperidinylidene-lower alkyl, such as 1-methylpiperidin-4-ylidenemethyl; 9-(lower alkyl)-3,9-diaza-bicyclo[3.3.1]non-3-yl-methyl; $C_3$-$C_8$-cycloalkyl; lower alkoxyphenyl; halo-phenyl, (lower-alkoxyphenyl)-phenyl; amino, N-lower alkylamino, N,N-di-lower alkylamino, N-lower alkanoylamino, N,N-di-lower alkanoylamino, hydroxy, lower alkoxy, phenoxy, piperidin-yloxy, N-lower alkyl-piperidinyl-oxy, halo, halo-lower alkoxy, lower alkanoyl, lower alkanoyl-oxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halo, or unsubstituted or substituted heterocyclyl, especially morpholinyl, piperazinyl, lower-alkylpiperazinyl, piperidinyl, N-lower alkyl-piperidinyl, pyrrolidinyl, N-mono- or N,N-Di-(lower alkyl)amino-pyrrolidinyl. Unsubstituted aryl is a corresponding aryl as just defined, but without substituent.

Unsubstituted or substituted heterocyclyl is preferably a saturated, partially saturated or unsaturated mono- or bicyclic or bicycle radical having from 4 to 10 ring members and from 1 to 3 heteroatoms which are preferably selected from nitrogen, oxygen and sulfur, e.g. pyrrolidinyl, 2H-pyrazolyl, pyridyl, piperidinyl, piperazinyl, morpholinyl, thiomorpholinyl or 3,9-diaza-bicyclo[3.3.1]non-3-ylmethyl, said radical being unsubstituted or substituted by one or more, preferably by one or two, independently selected radicals such as e.g. unsubstituted or substituted lower alkyl with substituents other than unsubstituted or substituted heterocyclyl, $C_3$-$C_8$-cyclopropyl, especially cyclopropyl, by halo-phenyl, (lower-alkoxyphenyl)-phenyl or lower alkoxy-phenyl, amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio or halo.

In lower alkyl-carbonyl, wherein the lower alkyl moiety is optionally substituted, the substituents if present are preferably one or more selected from those given for substituted lower alkyl. Preferred is $C_2$-$C_8$-alkanoyl, such as acetyl.

In lower alkoxy-carbonyl, wherein the lower alkyl moiety is optionally substituted, the substituents if present are preferably one or more selected from those given for substituted lower alkyl. Preferred is lower alkoxycarbonyl, such as methoxycarbonyl, isobutoxycarbonyl or tert-butoxycarbonyl.

In lower alkylsulfonyl (=lower alkyl-S(=O)$_2$)—), wherein the lower alkyl moiety is optionally substituted, the substituents if present are preferably one or more selected from those given for substituted lower alkyl. Preferred is lower alkylsulfonyl, such as methanesulfonyl.

In unsubstituted or substituted arylsulfonyl, unsubstituted or substituted aryl is preferably as defined above.

In N-mono- or N,N-di-(substituted amino)-carbonyl (=N-mono- or N,N-di-substituted carbamoyl), N-mono- or N,N-di-substituted amino is preferably as defined above. Preferred is N-lower alkylaminocarbonyl, such as methylcarbamoyl.

In lower alkoxy, wherein the lower alkyl moiety is optionally substituted, the substituents if present are preferably one or more selected from those given for substituted lower alkyl. Preferred is lower alkoxy, such as methoxy.

$R_7$ is preferably H.

Y is preferably O, S, S(=O), S(=O)$_2$ or CH$_2$, most preferably O.

Z is preferably C.

W is preferably absent (that is, $R_2$ is directly bound to NH in formula I).

$R_1$ is preferably halo, especially chloro, amino, lower alkylamino, e.g. methylamino, lower alkoxycarbonylamino, e.g. methoxy-, isobutoxy or tert-butoxy-carbonylamino, $C_2$-$C_8$-alkanoylamino, e.g. acetylamino, hydrazine, N—(N-mono- or N,N-di-loweralkylamino)-alkyl-amino, such as N-[2-(N,N-dimethylamino)-ethyl]-amino or N-[3-(N,N-dimethylamino)-propyl]-amino, hydroxyl, lower-alkoxy, such as methoxy, hydroxymethyl or lower-alkoxymethyl, such as methoxymethyl.

$R_2$ is preferably a cyclohexyl, phenyl, 2H-pyrazolyl or pyridyl, especially a phenyl, radical wherein said radical is substituted by one or more, especially 1 or 2, substituents independently selected from the group consisting of lower alkyl, such as methyl, ethyl, isopropyl or tert-butyl; halo-lower alkyl, such as especially trifluoromethyl or difluoroethyl; cyclopropyl; lower alkoxyphenyl, such as 4-methoxyphenyl; halo-phenyl, such as 4-fluorophenyl; (lower-alkoxyphenyl)-phenyl, such as 4-(4-methoxyphenyl)phenyl; lower alkoxy, especially methoxy; phenoxy; piperidinyl-oxy, such as piperidin-4-yloxy; N-lower alkyl-piperidinyl-oxy, such as 1-methylpiperidin-4-yloxy; halo; halo-lower alkoxy, such as trifluoromethoxy; morpholinyl, such as especially morpholin-4-yl; morpholinyl-lower alkyl, such as especially morpholin-4-ylmethyl; piperazinyl-lower alkyl; lower alkyl-piperazinyl-lower alkyl, such as especially 4-methylpiperazin-1-ylmethyl; piperidinyl-lower alkyl, such as piperidin-4-ylmethyl; N-lower alkyl-piperidinyl-lower alkyl; such as 1-methylpiperidin-4-ylmethyl; pyrrolidinyl, N-mono- or N,N-Di-(lower alkyl)amino-pyrrolidinyl; such as 3-(N,N-dimethylamino)-pyrrolidin-1-yl; piperidinyliden-lower alkyl, such as piperidin-4-ylidenemethyl; and N-lower alkyl-piperidinylidene-lower alkyl, such as 1-methylpiperidin-4-ylidenemethyl.

$R_2$ is very preferably phenyl substituted by one or two substituents selected from the group consisting of F, Cl, $CF_3$, $OCF_3$, $CHF_2$, $CF_2CH_3$, methyl, ethyl, propyl, tert-butyl, phenoxy, halogen, methylpiperazinyl methyl, methoxy, cyclopropyl, methylpiperidinyl methyl and 4-methylimidazol-1-yl.

Preferred is a compound of the formula I wherein one of A and B is N, the other and X are CH, respectively.

In a preferred embodiment the present invention relates to a compound of the formula I wherein $R_1$ is H; chloro, $CH_2OH$, $CH_2OCH_2$ phenyl, $NH_2$, $NHNH_2$, $NHCH_3$ or $NHCOOCH_3$;

$R_2$ is phenyl substituted by one or two substituents selected from the group consisting of halo $C_{1-7}$alkyl, trifluoromethoxy, $C_{1-7}$ alkyl, phenoxy, halogen, $C_{1-7}$ alkylpiperazinyl $C_{1-7}$alkyl, $C_{1-7}$alkyl, $C_{1-7}$ alkoxy, $C_3$-$C_8$-cycloalkyl, $C_{1-7}$alkylpiperidinyl $C_{1-7}$alkyl and $C_{1-7}$alkylimidazolyl;

A, B and X are independently selected from $C(R_7)$ or N, with the proviso that not more than one of A, B and X is N;

$R_7$ is hydrogen;

$R_8$ is hydrogen;

$R_9$ is a substituent;

n is 0;

Y is O;

Z is C;

W is absent;

K is N or C, and either a), if K is C, the bond indicated by the waved line ( ~~~ ) is a double bond, Q is selected from

O—N

S—N

O—CH and

S—CH where in each case the left O or S atom is bound by the bond shown in formula I to K, the right N or carbon atom (of CH) to C via the bond indicated by the broken line ( ------ ) in formula I, with the proviso that said bond indicated by the broken line is a double bond to C;

and the bond represented in bold ( — ) is a single bond;

or b), if K is N, the bond indicated by the waved line is a single bond,

Q is

N═CH where the left N atom is bound by the bond shown in formula I to K, the right carbon atom (of CH) to C via the bond indicated by the broken line in formula I, with the proviso that said bond indicated by the broken line is a single bond to C;

and the bond represented in bold is a double bond;

or a tautomer thereof, and/or a (preferably pharmaceutically acceptable) salt thereof.

In a preferred embodiment the present invention relates to a compound of the formula IA

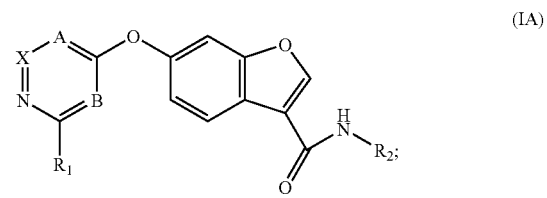

(IA)

wherein X, A, B, $R_1$, and $R_2$ are as defined above.

In a preferred embodiment the present invention relates to a compound of the formula IB,

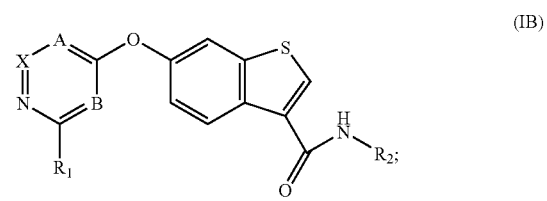

(IB)

wherein X, A, B, $R_1$, and $R_2$ are as defined above.

In a preferred embodiment the present invention relates to a compound of the formula IC,

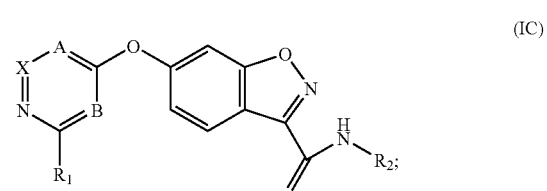

(IC)

wherein X, A, B, $R_1$, and $R_2$ are as defined above.

In a preferred embodiment the present invention relates to a compound of the formula ID,

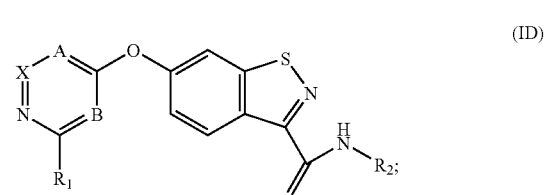

(ID)

wherein X, A, B, $R_1$, and $R_2$ are as defined above.

In a preferred embodiment the present invention relates to a compound of the formula IE,

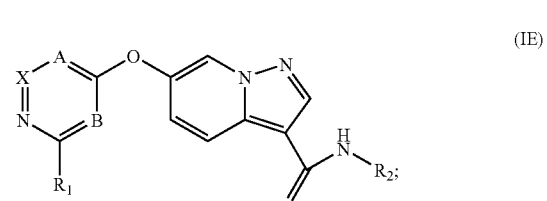

(IE)

wherein X, A, B, Y, W, $R_1$ and $R_2$ are as defined above.

In a preferred embodiment the present invention relates to a compound selected from the group consisting of 6-(2-chloro-pyrimidin-4-yloxy)-benzo[d]isoxazole-3-carboxylic acid (3-trifluoromethyl-phenyl)-amide,
6-(2-hydrazino-pyrimidin-4-yloxy)-benzo[d]isoxazole-3-carboxylic acid (3-trifluoromethyl-phenyl)-amide,
6-(2-methylamino-pyrimidin-4-yloxy)-benzo[d]isoxazole-3-carboxylic acid (3-trifluoromethyl-phenyl)-amide,
6-(pyrimidin-4-yloxy)-benzo[d]isoxazole-3-carboxylic acid (4-fluoro-3-trifluoromethyl-phenyl)-amide,
{4-[3-(3-trifluoromethyl-phenylcarbamoyl)-benzo[d]isoxazol-6-yloxy]-pyrimidin-2-yl}-carbamic acid tert-butyl ester,
6-(2-amino-pyrimidin-4-yloxy)-benzo[d]isoxazole-3-carboxylic acid (3-trifluoromethyl-phenyl)-amide, a tautomer thereof and/or a pharmaceutically acceptable salt thereof.

In a preferred embodiment the present invention relates to a compound selected from the group consisting of 6-(2-amino-pyrimidin-4-yloxy)-benzo[d]isothiazole-3-carboxylic acid (4-fluoro-3-trifluoromethyl-phenyl)-amide
(4-{3-[4-(4-Methyl-piperazin-1-ylmethyl)-3-trifluoromethyl-phenylcarbamoyl]-benzo[d]isothiazol-6-yloxy}-pyrimidin-2-yl)-carbamic acid methyl ester,
6-(2-amino-pyrimidin-4-yloxy)-benzo[d]isothiazole-3-carboxylic acid [4-(4-methyl-piperazin-1-ylmethyl)-3-trifluoromethyl-phenyl]-amide, a tautomer thereof and/or a pharmaceutically acceptable salt thereof.

In a preferred embodiment the present invention relates to a compound selected from the group consisting of 6-(2-amino-pyrimidin-4-yloxy)-benzofuran-3-carboxylic acid (4-fluoro-3-trifluoromethyl-phenyl)-amide,
6-(2-Amino-pyrimidin-4-yloxy)-benzofuran-3-carboxylic acid (3-trifluoromethyl-phenyl)-amide,
6-(2-Amino-pyrimidin-4-yloxy)-benzofuran-3-carboxylic acid (3-trifluoromethoxy-phenyl)-amide,
6-(2-Amino-pyrimidin-4-yloxy)-benzofuran-3-carboxylic acid (3-cyclopropyl-phenyl)-amide,
6-(2-Amino-pyrimidin-4-yloxy)-benzofuran-3-carboxylic acid (3-isopropyl-phenyl)-amide,
6-(2-Amino-pyrimidin-4-yloxy)-benzofuran-3-carboxylic acid (3,4-dimethyl-phenyl)-amide,
6-(2-Amino-pyrimidin-4-yloxy)-benzofuran-3-carboxylic acid (3,5-dimethoxy-phenyl)-amide,
6-(2-Amino-pyrimidin-4-yloxy)-benzofuran-3-carboxylic acid (4-methyl-3-trifluoromethyl-phenyl)-amide,
6-(2-Amino-pyrimidin-4-yloxy)-benzofuran-3-carboxylic acid (3-tert-butyl-phenyl)-amide,
6-(2-Amino-pyrimidin-4-yloxy)-benzofuran-3-carboxylic acid (3-phenoxy-phenyl)-amide, and
6-(2-Amino-pyrimidin-4-yloxy)-benzofuran-3-carboxylic acid [4-(4-methyl-piperazin-1-ylmethyl)-3-trifluoromethyl-phenyl]-amide,
(4-{3-[4-(4-methyl-piperazin-1-ylmethyl)-3-trifluoromethyl-phenylcarbamoyl]-benzofuran-6-yloxy}-pyrimidin-2-yl)-carbamic acid methyl ester
6-(6-Benzyloxymethyl-pyrimidin-4-yloxy)-benzofuran-3-carboxylic acid (3-trifluoromethyl-phenyl)-amide,
6-(6-Hydroxymethyl-pyrimidin-4-yloxy)-benzofuran-3-carboxylic acid (3-trifluoromethyl-phenyl)-amide,
6-(6-benzyloxymethyl-pyrimidin-4-yloxy)-benzofuran-3-carboxylic acid (3-tert-butyl-phenyl)-amide,
6-(6-hydroxymethyl-pyrimidin-4-yloxy)-benzofuran-3-carboxylic acid (3-tert-butyl-phenyl)-amide,
6-(6-benzyloxymethyl-pyrimidin-4-yloxy)-benzofuran-3-carboxylic acid (3-trifluoromethoxy-phenyl)-amide,
6-(6-hydroxymethyl-pyrimidin-4-yloxy)-benzofuran-3-carboxylic acid (3-trifluoromethoxy-phenyl)-amide,
6-(6-benzyloxymethyl-pyrimidin-4-yloxy)-benzofuran-3-carboxylic acid (3-cyclopropyl)-amide,
6-(6-hydroxymethyl-pyrimidin-4-yloxy)-benzofuran-3-carboxylic acid (3-cyclopropyl)-amide,
6-(6-benzyloxymethyl-pyrimidin-4-yloxy)-benzofuran-3-carboxylic acid [3-(1,1-difluoro-ethyl)-phenyl]-amide,
6-(6-hydroxymethyl-pyrimidin-4-yloxy)-benzofuran-3-carboxylic acid [3-(1,1-difluoro-ethyl)-phenyl]-amide,
6-(6-benzyloxymethyl-pyrimidin-4-yloxy)-benzofuran-3-carboxylic acid [4-(1-methyl-piperidin-4-ylmethyl)-3-trifluoromethyl-phenyl]-amide,
6-(6-hydroxymethyl-pyrimidin-4-yloxy)-benzofuran-3-carboxylic acid [4-(1-methyl-piperidin-4-ylmethyl)-3-trifluoromethyl-phenyl]-amide,
6-(6-benzyloxymethyl-pyrimidin-4-yloxy)-benzofuran-3-carboxylic acid [3-(4-methyl-imidazol-1-yl)-5-trifluoromethyl-phenyl]-amide,
6-(6-hydroxymethyl-pyrimidin-4-yloxy)-benzofuran-3-carboxylic acid [3-(4-methyl-imidazol-1-yl)-5-trifluoromethyl-phenyl]-amide, a tautomer thereof and/or a pharmaceutically acceptable salt thereof.

In a preferred embodiment the present invention relates to a compound selected from the group consisting of 6-(2-amino-pyrimidin-4-yloxy)-benzo[b]thiophene-3-carboxylic acid (3-trifluoromethyl-phenyl)-amide
6-(2-amino-pyrimidin-4-yloxy)-benzo[b]thiophene-3-carboxylic acid (4-fluoro-3-trifluoromethyl-phenyl)-amide,
6-(2-amino-pyrimidin-4-yloxy)-benzo[b]thiophene-3-carboxylic acid (3-trifluoromethoxy-phenyl)-amide,
6-(2-amino-pyrimidin-4-yloxy)-benzo[b]thiophene-3-carboxylic acid (3-cyclopropyl-phenyl)-amide,
6-(2-amino-pyrimidin-4-yloxy)-benzo[b]thiophene-3-carboxylic acid (3-isopropyl-phenyl)-amide,
6-(2-amino-pyrimidin-4-yloxy)-benzo[b]thiophene-3-carboxylic acid (4-tert-butyl-phenyl)-amide,
6-(2-amino-pyrimidin-4-yloxy)-benzo[b]thiophene-3-carboxylic acid (3,4-dimethyl-phenyl)-amide,
6-(2-amino-pyrimidin-4-yloxy)-benzo[b]thiophene-3-carboxylic acid (3,5-dimethoxy-phenyl)-amide,
6-(2-amino-pyrimidin-4-yloxy)-benzo[b]thiophene-3-carboxylic acid (4-methyl-3-trifluoromethyl-phenyl)-amide,
6-(2-amino-pyrimidin-4-yloxy)-benzo[b]thiophene-3-carboxylic acid (3-tert-butyl-phenyl)-amide,
6-(2-amino-pyrimidin-4-yloxy)-benzo[b]thiophene-3-carboxylic acid (3-phenoxy-phenyl)-amide,
6-(2-amino-pyrimidin-4-yloxy)-benzo[b]thiophene-3-carboxylic acid [4-(4-methyl-piperazin-1-ylmethyl)-3-trifluoromethyl-phenyl]-amide,
(4-{3-[4-(4-methyl-piperazin-1-ylmethyl)-3-trifluoromethyl-phenylcarbamoyl]-benzo[b]thiophene-6-yloxy}-pyrimidin-2-yl)-carbamic acid methyl ester; and
6-(2-amino-pyrimidin-4-yloxy)-pyrazolo[1,5-a]pyridine-3-carboxylic acid (3-trifluoromethyl-phenyl)-amide,
6-(2-amino-pyrimidin-4-yloxy)-pyrazolo[1,5-a]pyridine-3-carboxylic acid (4-fluoro-3-trifluoromethyl-phenyl)-amide,
6-(2-amino-pyrimidin-4-yloxy)-pyrazolo[1,5-a]pyridine-3-carboxylic acid (3-trifluoromethoxy-phenyl)-amide, 6-(2-amino-pyrimidin-4-yloxy)-pyrazolo[1,5-a]pyridine-3-carboxylic acid (4-chlor-3-trifluoromethyl-phenyl)-amide, 6-(2-amino-pyrimidin-4-yloxy)-pyrazolo[1,5-a]pyridine-3-carboxylic acid (3-tert-butyl-phenyl)-amide, 6-(2-amino-pyrimidin-4-yloxy)-pyrazolo[1,5-a]pyridine-3-carboxylic acid [4-(4-methyl-piperazin-1-ylmethyl)-3-trifluoromethyl-phenyl]-amide, 6-(2-amino-pyrimidin-4-yloxy)-pyrazolo[1,5-a]pyridine-3-carboxylic acid (3-cyclopropyl-phenyl)-amide, 6-(2-amino-pyrimidin-4-yloxy)-pyrazolo[1,5-a]pyridine-3-carboxylic acid (3,5-dimethoxy-phenyl)-amide, 6-(2-Hydroxymethyl-pyrimidin-4-yloxy)-benzo[b]thiophene-3-carboxylic acid (3-tert-butyl-phenyl)-amide, 6-(2-Hydroxymethyl-pyrimidin-4-yloxy)-benzo[b]thiophene-3-carboxylic acid (3-trifluoromethyl-phenyl)-amide, 6-(2-Hydroxymethyl-pyrimidin-4-yloxy)-benzo[b]thiophene-3-carboxylic acid (3-trifluoromethoxy-phenyl)-amide, 6-(2-Hydroxymethyl-pyrimidin-4-yloxy)-benzo[b]thiophene-3-carboxylic acid (3-cyclopropyl-phenyl)-amide, 6-(2-Hydroxymethyl-pyrimidin-4-yloxy)-benzo[b]thiophene-3-carboxylic acid (3-isopropyl-phenyl)-amide, 6-(2-Hydroxymethyl-pyrimidin-4-yloxy)-benzo[b]thiophene-3-carboxylic acid [3-(1,1-difluoro-ethyl)-phenyl]-amide, 6-(2-Hydroxymethyl-pyrimidin-4-yloxy)-benzo[b]thiophene-3-carboxylic acid (4-methyl-3-trifluoromethyl-phenyl)-amide, 6-(2-Hydroxymethyl-pyrimidin-4-yloxy)-benzo[b]thiophene-3-carboxylic acid (4-tert-butyl-phenyl)-amide, 6-(2-Hydroxymethyl-pyrimidin-4-yloxy)-benzo[b]thiophene-3-carboxylic acid [4-(1-methyl-piperidin-4-ylmethyl)-3-trifluoromethyl-phenyl]-amide, 6-(6-Hydroxymethyl-pyrimidin-4-yloxy)-benzo[b]thiophene-3-carboxylic acid (4-fluoro-3-trifluoromethyl-phenyl)-amide, 6-(6-Hydroxymethyl-pyrimidin-4-yloxy)-benzo[b]thiophene-3-carboxylic acid (3-trifluoromethyl-phenyl)-amide, 6-(6-Hydroxymethyl-pyrimidin-4-yloxy)-benzo[b]thiophene-3-carboxylic acid (3-trifluoromethoxy-phenyl)-amide, 6-(6-Hydroxymethyl-pyrimidin-4-yloxy)-benzo[b]thiophene-3-carboxylic acid (3-cyclopropyl-phenyl)-amide, 6-(6-Hydroxymethyl-pyrimidin-4-yloxy)-benzo[b]thiophene-3-carboxylic acid (3-tert-butyl-phenyl)-amide, 6-(6-Hydroxymethyl-pyrimidin-4-yloxy)-benzo[b]thiophene-3-carboxylic acid (4-tert-butyl-phenyl)-amide, 6-(6-Hydroxymethyl-pyrimidin-4-yloxy)-benzo[b]thiophene-3-carboxylic acid [4-methyl-3-trifluoromethyl-phenyl]-amide, 6-(6-Hydroxymethyl-pyrimidin-4-yloxy)-benzo[b]thiophene-3-carboxylic acid [4-(1-methyl-piperidin-4-ylmethyl)-3-trifluoromethyl-phenyl]-amide, a tautomer thereof and/or a pharmaceutically acceptable salt thereof.

The present invention also relates to compounds of formula I

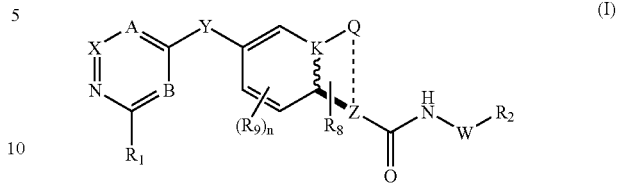

(I)

wherein $R_1$ is H; halo; lower alkyl; cyano; —$C_0$-$C_7$—O—$R_3$; —$C_0$-$C_7$—$NR_4R_5$; or —C(=O)—$R_6$;

$R_2$ is substituted $C_3$-$C_8$-cycloalkyl; substituted aryl; or substituted heterocyclyl;

$R_3$ is H, unsubstituted or substituted lower alkyl or unsubstituted or substituted lower alkylcarbonyl;

$R_4$ and $R_5$ are independently selected from the group consisting of H; unsubstituted or substituted lower alkyl; lower alkyl-carbonyl, wherein the lower alkyl moiety is optionally substituted; lower alkoxy-carbonyl, wherein the lower alkyl moiety is optionally substituted, lower alkylsulfonyl, wherein the lower alkyl moiety is optionally substituted, unsubstituted or substituted arylsulfonyl, and N-mono- or N,N-di-(substituted amino)-carbonyl; or one is unsubstituted or substituted amino, the other is one of the other moieties mentioned for $R_4$ and $R_5$;

$R_6$ is H; OH; unsubstituted or substituted lower alkyl; lower alkoxy, wherein the lower alkyl moiety is optionally substituted; or unsubstituted, mono- or di-substituted amino;

A, B and X are independently selected from C($R_7$) or N, with the proviso that not more than one of A, B and X is N;

$R_7$ is selected from the group consisting of H, halo and unsubstituted or substituted lower alkyl;

$R_8$ is hydrogen or lower alkyl;

$R_9$ is a substituent;

n is 0, 1, 2 or 3, preferably 0;

Y is O, S, S(O), S(O)$_2$, CH$_2$, CH$_2$—CH$_2$, CH=CH or C≡C;

Z is N or CH;

W is absent or is lower alkylene, especially CH$_2$, CH$_2$—CH$_2$ or CH$_2$—CH$_2$—CH$_2$;

K is N or C, and either a), if K is C, the bond indicated by the waved line ( ~~~ ) is a double bond, Q is selected from

O—N

S—N

O—CH and

S—CH where in each case the left O or S atom is bound by the bond shown in formula I to K, the right N or carbon atom (of CH) to Z via the bond indicated by the broken line ( ------- ) in formula I, with the proviso that said bond indicated by the broken line is a double bond to Z;

and the bond represented in bold ( ▬ ) is a single bond;

or b), if K is N, the bond indicated by the waved line is a single bond,

Q is

N=CH where the left N atom is bound by the bond shown in formula I to K, the right carbon atom (of CH) to Z via the bond indicated by the broken line in formula I, with the proviso that said bond indicated by the broken line is a single bond to Z;

and the bond represented in bold is a double bond;

or a tautomer thereof, and/or a salt thereof.

The present invention also relates to compounds of formula IAA

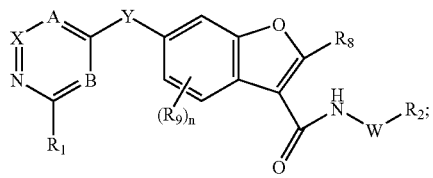

(IAA)

wherein X, A, B, Y, W, $R_1$, $R_2$, $R_8$, $R_9$ and n are as defined above, a tautomer thereof and/or a salt thereof.

The present invention also relates to compounds of formula IBB,

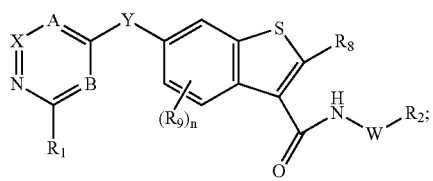

(IBB)

wherein X, A, B, Y, W, $R_1$, $R_2$, $R_8$, $R_9$ and n are as defined above, a tautomer thereof and/or a salt thereof.

The present invention also relates to compounds of formula ICC,

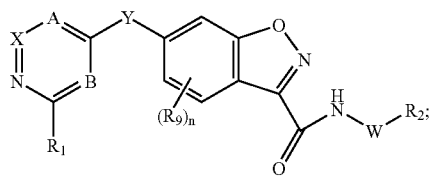

(ICC)

wherein X, A, B, Y, W, $R_1$, $R_2$, $R_9$ and n are as defined above, a tautomer thereof and/or a salt thereof.

The present invention also relates to compounds of formula IDD,

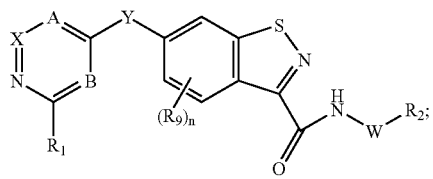

(IDD)

wherein X, A, B, Y, W, $R_1$, $R_2$, $R_9$ and n are as defined above, a tautomer thereof and/or a salt thereof.

The present invention also relates to compounds of formula IEE,

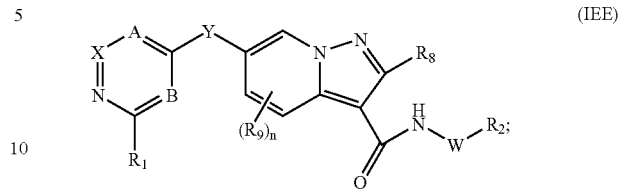

(IEE)

wherein X, A, B, Y, W, $R_1$ and $R_2$ are as defined above, a tautomer thereof and/or a salt thereof.

The present invention also relates to compounds of formula I wherein $R_1$ is halo, lower alkyl, cyano, amino, lower alkylamino, lower alkanoylamino, lower alkoxycarbonylamino, lower alkylsulfonylamino, N-mono- or N,N-di-(lower alkyl) amino-carbonyl-amino, hydrazino, N-mono-or N,N-di-(loweralkyl)-hydrazino, amino-lower alkylamino, N-(mono- or di-loweralkyl)amino-lower alkyl-amino, hydroxy-lower alkyl or lower-alkoxy-lower alkyl, $R_2$ is phenyl substituted by one or two substituents independently selected from lower alkyl, halo-lower alkyl, morpholinyl-lower alkyl, piperazinyl-lower alkyl, lower alkyl-piperazinyl-lower alkyl, $C_3$-$C_8$-cycloalkylpiperazinyl, piperidinyl-lower alkyl, N-lower alkyl-piperidinyl-lower alkyl, piperidinyliden-lower alkyl or N-lower alkyl-piperidinylidene-lower alkyl, such as 1-methylpiperidin-4-ylidenemethyl; 9-(lower alkyl)-3,9-diaza-bicyclo[3.3.1] non-3-yl-methyl; $C_3$-$C_8$-cycloalkyl; lower alkoxyphenyl; halo-phenyl, (lower-alkoxyphenyl)-phenyl; amino, N-lower alkylamino, N,N-di-lower alkylamino, N-lower alkanoylamino, N,N-di-lower alkanoylamino, hydroxy, lower alkoxy, phenoxy, piperidinyloxy, N-lower alkyl-piperidinyl-oxy, halo, halo-lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halo, or unsubstituted or substituted heterocyclyl selected from the group consisting of morpholinyl, piperazinyl, lower-alkylpiperazinyl, piperidinyl, N-lower alkyl-piperidinyl, pyrrolidinyl, N-mono- or N,N-Di-(lower alkyl)amino-pyrrolidinyl; or $R_2$ is 2H-pyrazolyl that is unsubstituted or substituted by lower alkyl and by halo-phenyl, (lower-alkoxyphenyl)-phenyl or lower alkoxy-phenyl;

A is CH or N and B is CH or N, with the proviso that nor more than one of A and B is N;

X is CH;

Y is O, S, S(O), S(O)$_2$, CH$_2$, CH$_2$—CH$_2$, CH=CH or C≡C, preferably O or S;

$R_8$ is hydrogen or lower alkyl, preferably hydrogen;

a tautomer thereof and/or a pharmaceutically acceptable salt thereof.

Where the plural form is used for compounds, salts, pharmaceutical compositions, diseases and the like, this is intended to mean also a single compound, salt, or the like.

In view of the close relationship between the compounds of formula I in free form and in the form of their salts, including those salts that can be used as intermediates, for example in the purification or identification of the compounds of formula I, tautomers or tautomeric mixtures and their salts, any reference hereinbefore and hereinafter to these compounds is to be understood as referring also to the corresponding tautomers of these compounds, tautomeric mixtures of these compounds, N-oxides of these compounds, or salts of any of these, as appropriate and expedient and if not mentioned otherwise. Tautomers can, e.g., be present in cases where amino or hydroxy are bound to carbon atoms that are bound to adjacent atoms by double bonds (e.g. keto-enol or imine-enamine tautomerism).

Asymmetric carbon atoms of a compound of formula I that are optionally present may exist in the (R), (S) or (R,S) configuration, preferably in the (R) or (S) configuration. Substituents at a double bond or a ring may be present in cis-(=Z—) or trans (=E-) form. The compounds may thus be present as mixtures of isomers or preferably as pure isomers.

Salts are preferably the pharmaceutically acceptable salts of the compounds of formula I.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts. For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The terms "treatment" or "therapy" refer to the prophylactic or preferably therapeutic (including but not limited to palliative, curing, symptom-alleviating, symptom-reducing, kinase-regulating and/or kinase-inhibiting) treatment of said diseases, especially of the diseases mentioned below.

Where subsequently or above the term "use" is mentioned (as verb or noun) (relating to the use of a compound of the formula I or a pharmaceutically acceptable salt thereof), this includes any one or more of the following embodiments of the invention, respectively: the use in the treatment of a protein kinase dependent disease, the use for the manufacture of pharmaceutical compositions for use in the treatment of a protein kinase dependent disease, methods of use of one or more compounds of the formula I in the treatment of a protein kinase dependent disease, the use of pharmaceutical preparations comprising one or more compounds of the formula I for the treatment of a protein kinase dependent disease, and one or more compounds of the formula I for use in the treatment of a protein kinase dependent disease, as appropriate and expedient and if not stated otherwise. In particular, diseases to be treated and are thus preferred for "use" of a compound of formula I are selected from protein kinase dependent ("dependent" meaning also "supported", not only "solely dependent") diseases mentioned herein, especially proliferative diseases mentioned herein, more especially any one or more of these or other diseases that depend on one or more of c-Abl, Bcr-Abl, c-Kit, Raf kinases such as especially B-Raf, the rearranged during transfection (RET) proto-oncogene, Platelet-derived Growth Factor Receptors (PDGF-Rs), Lck, Hck and most especially the Vascular Endothelial Growth Factor Receptors (VEGF-Rs) such as in particular VEGF-R2, or a mutant of any one or more of these, and a compound of the formula I can therefore be used in the treatment of a kinase dependent disease, especially a disease depending on one or more of the kinases mentioned above and below, where (especially in the case of aberrantly highly-expressed, constitutively activated and/or mutated kinases) said kinase-dependent disease is dependent on the activity of one or more of the said kinases or the pathways they are involved.

The compounds of formula I have valuable pharmacological properties and are useful in the treatment of protein kinase dependent diseases, for example as drugs to treat proliferative diseases.

The efficacy of the compounds of formula I as inhibitors of c-Abl protein tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris.HCl, pH 7.5, 10 mM $MgCl_2$, 10 µM $Na_3VO_4$, 1 mM DTT and 0.06 µCi/assay [γ $^{33}$P]-ATP (5 µM ATP) using 30 µg/ml poly-Ala,Glu,Lys,Tyr-6:2:5:1 (Poly-AEKY, Sigma P1152) in the presence of 1% DMSO. Reactions are terminated by adding 10 µL of 250 mM EDTA and 30 µL of the reaction mixture is transferred onto Immobilon-PVDF membrane (Millipore, Bedford, Mass., USA) previously soaked for 5 min with MeOH, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, the compounds of formula I show $IC_{50}$ values of inhibition in the range of 0.001 to 100 µM, usually between 0.05 and 5 µM.

Bcr-Abl inhibition can be determined by a capture ELISA as follows: The murine myeloid progenitor cell line 32Dcl3 transfected with the p210 Bcr-Abl expression vector pGDp210Bcr/Abl (32D-bcr/abl) is obtained from J Griffin (Bazzoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The cells are expanded in RPMI 1640 (AMIMED; cat #1-41F01), 10% fetal calf serum, 2 mM glutamine (Gibco) ("complete medium"), and a working stock is prepared by freezing aliquots of $2\times10^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. # 06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. # 03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (ST1571) (marketed as Gleevec® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 μM followed by preparation of serial threefold dilutions in complete medium. No solubility problems are encountered using this procedure. The test compounds of formula I are treated analogously. For the assay, 200'000 32D-bcr/abl cells in 50 μl are seeded per well in 96 well round bottom tissue culture plates. 50 μl per well of serial threefold dilutions of the test compound are added to the cells in triplicates. The final concentration of the test compound range e.g. from 5 μM down to 0.01 μM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 μl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 μg/ml aprotinin and 80 μg/ml leupeptin) and either used immediately for the ELISA or stored frozen at −20° C. until usage. The anti-abl SH3 domain antibody is coated at 200 ng in 50 μl PBS per well to black ELISA plates (Packard HTRF-96 black plates; 6005207) overnight at 4° C. After washing 3× with 200 μl/well PBS containing 0.05% Tween 20 (PBST) and 0.5% TopBlock (Juro, Cat. # TB 232010), residual protein binding sites are blocked with 200 μl/well PBST, 3% TopBlock for 4 h at room temperature, followed by incubation with 50 μl lysates of untreated or test compound-treated cells (20 μg total protein per well) for 3-4 h at 4° C. After 3× washing, 50 μl/well PY20(AP) (Zymed) diluted to 0.5 μg/ml in blocking buffer is added and incubated over-night (4° C.). For all incubation steps, the plates are covered with plate sealers (Costar, cat. # 3095). Finally, the plates are washed another three times with washing buffer and once with deionized water before addition of 90 μl/well of the AP substrate CPD-Star RTU with Emerald II. The plates now sealed with Packard Top Seal™-A plate sealers (cat. # 6005185) are incubated for 45 min at room temperature in the dark and luminescence is quantified by measuring counts per second (CPS) with a Packard Top Count Microplate Scintillation Counter (Top Count). For the final optimized version of the ELISA, 50 μl of the lysates of the cells grown, treated and lysed in 96 well tissue culture plates, are transferred directly from these plates to the ELISA plates that are precoated with 50 ng/well of the rabbit polyclonal ant-abl-SH3 domain AB 06-466 from Upstate. The concentration of the anti-phosphotyrosine AB PY20 (AP) can be reduced to 0.2 μg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation. The compounds of formula I here show $IC_{50}$ values in the range from 10 nM to 20 μM.

The efficacy of the compounds of formula I as inhibitors of c-Kit and PDGF-R tyrosine kinase activity can be demonstrated as follows:

BaF3-Tel-PDGFRbeta and BaF3-KitD816V are BaF3 murine proB-cell lymphoma cell derivatives [the BaF3 cell line is available from the German Collection of Microorganisms and Cell Cultures (DSMZ), Braunschweig, Germany] that have been rendered IL-3-independent by stable transduction with Tel-fusion-activated PDGFβ-R wild-type (Golub T. R. et al., Cell 77(2): 307-316, 1994) or D816V-mutation-activated c-kit, respectively. Cells are cultured in RPMI-1640 (Animed # 1-14F01-I) supplemented with 2% L-glutamine (Animed # 5-10K50-H) and 10% fetal calf serum (FCS, Animed # 2-01F16-I). Wild-type, untransfected BaF3 cells are maintained in above medium plus 10 U/ml IL-3 (mouse Interleukin-3, Roche # 1380745). Cells are diluted in fresh medium to a final density of $3\times10^5$ cells per ml and 50 μl aliquots seeded into 96-well plates ($1.5\times10^4$ cells per well). 50 μl 2× compound solutions are added. As internal control, the kinase inhibitor PKC412 is routinely used. Control cells treated with DMSO (0.1% final concentration) serve as growth reference (set as 100% growth). In addition, a plate blank value is routinely determined in a well containing only 100 μl of medium and no cells. $IC_{50}$ determinations are performed based on eight 3-fold serial dilutions of the test compound, starting at 10 μM. Following incubation of the cells for 48 h at 37° C. and 5% $CO_2$, the effect of inhibitors on cell viability is assessed by the resazurin sodium salt dye reduction assay (commercially known as AlamarBlue assay) basically as previously described (O'Brien J. et al., Eur. J. Biochem. 267: 5421-5426, 2000). 10 μl of AlamarBlue is added per well and the plates incubated for 6 h at 37° C. and 5% $CO_2$. Thereafter, fluorescence is measured using a Gemini 96-well plate reader (Molecular Devices) with the following settings: Excitation 544 nm and Emission 590 nm. Acquired raw data are exported to Excel-file format. For data analysis, the plate blank value is subtracted from all data points. The anti-proliferative effect of a compound by the AlamarBlue read-out was then calculated as percentage of the value of the control cells set as 100%. $IC_{50}$ values are determined using XLfit software program. The compounds of formula I show an $IC_{50}$ for c-Kit and PDGFβ-R in the range of 0.001 to 20 μM, especially between 0.001 and 0.1 μM.

Active Raf kinases, such as active B-Raf protein, of human sequence are purified from insect cells using the baculoviral expression system. Raf inhibition is tested in 96-well microplates coated with IκB-α and blocked with Superblock. The phosphorylation of IκB-α at Serine 36 is detected using a phospho-IκB-α specific antibody (Cell Signaling #9246), an anti-mouse IgG alkaline phosphatase conjugated secondary antibody (Pierce # 31320), and an alkaline phosphatase substrate, ATTOPHOS (Promega, #S101).

RET kinase inhibition is determined as follows:

Cloning and expression: The baculovirus donor vector pFB-GSTX3 is used to generate a recombinant baculovirus that expresses the amino acid region 658-1072 (Swiss prot No. Q9BTB0) of the cytoplasmic kinase domain of human RET-Men2A which corresponds to the wild-type kinase domain of RET (wtRET) and RET-Men2B, which differs from the wtRET by the activating mutation in the activation loop M918T. The coding sequence for the cytoplasmic domain of wtRET is amplified by PCR from a cDNA library using specific primers. RET-Men2B is generated through site-directed mutagenesis resulting in the M918T mutation. The amplified DNA fragments and the pFB-GSTX3 vector are made compatible for ligation by digestion with SalI and KpnI. Ligation of these DNA fragments results in the baculovirus donor plasmids pFB-GX3-RET-Men2A and pFB-GX3-RET-Men2B, respectively.

Production of virus: The baculovirus donor plasmids containing the kinase domains are transfected into the DH10Bac cell line (GIBCO) and the transfected cells are plated on selective agar plates. Colonies without insertion of the fusion sequence into the viral genome (carried by the bacteria) are blue. Single, white colonies are picked and viral DNA (bacmid) is isolated from the bacteria by standard plasmid purification procedures. Sf9 cells or Sf21 cells (American Type Culture Collection) are then transfected in 25 cm² flasks with the viral DNA using Cellfectin reagent.

Protein expression in Sf9 cells: Virus-containing media is collected from the transfected cell culture and used for infection to increase its titer. Virus-containing media obtained after two rounds of infection is used for large-scale protein expression. For large-scale protein expression 100 cm² round tissue culture plates are seeded with $5 \times 10^7$ cells/plate and infected with 1 ml of virus-containing media (approximately 5 MOIs). After 3 days, the cells are scraped off the plate and centrifuged at 500 rpm for 5 minutes. Cell pellets from 10-20, 100 cm² plates are re-suspended in 50 ml of ice-cold lysis buffer (25 mM Tris-HCl, pH 7.5, 2 mM EDTA, 1% NP-40, 1 mM DTT, 1 mM PMSF). The cells are stirred on ice for 15 minutes and then centrifuged at 5,000 rpms for 20 minutes.

Purification of GST-tagged proteins: The centrifuged cell lysate is loaded onto a 2 ml glutathione-sepharose column (Pharmacia) and washed 3× with 10 ml of 25 mM Tris-HCl, pH 7.5, 2 mM EDTA, 1 mM DTT, 200 mM NaCl. The GST-tagged proteins are then eluted by 10 applications (1 ml each) of 25 mM Tris-HCl, pH 7.5, 10 mM reduced-glutathione, 100 mM NaCl, 1 mM DTT, 10% glycerol and stored at −70° C.

Measure of enzyme activity: Tyrosine protein kinase assays with either purified GST-wtRET or GST-RET-Men2B protein are carried out in a final volume of 30 µL containing 15 ng of either GST-wtRET or GST-RET-Men2B protein, 20 mM Tris-HCl, pH 7.5, 1 mM MnCl$_2$, 10 mM MgCl$_2$, 1 mM DTT, 3 µg/ml poly(Glu,Tyr) 4:1, 1% DMSO, 2.0 µM ATP ($\gamma$-[$^{33}$P]-ATP 0.1 µCi). The activity is assayed in the presence or absence of inhibitors, by measuring the incorporation of $^{33}$P from [$\gamma^{33}$P] ATP into poly(Glu,Tyr) 4:1. The assay is carried out in 96-well plates at ambient temperature for 15 minutes under conditions described above and terminated by the addition of 20 µL of 125 mM EDTA. Subsequently, 40 µL of the reaction mixture are transferred onto Immobilon-PVDF membrane (Millipore) previously soaked for 5 minutes with MeOH, rinsed with water, then soaked for 5 minutes with 0.5% H$_3$PO$_4$ and mounted on vacuum manifold with disconnected vacuum source. After spotting all samples, vacuum is connected and each well rinsed with 200 µL 0.5% H$_3$PO$_4$. Membranes are removed and washed 4× on a shaker with 1.0% H$_3$PO$_4$, once with ethanol. Membranes are counted after drying at ambient temperature, mounting in Packard TopCount 96-well frame, and addition of 10 µL/well of Microscint™ (Packard). IC$_{50}$ values are calculated by linear regression analysis of the percentage inhibition of each compound in duplicate, at 4 concentrations (usually 0.01, 0.1, 1 and 10 µM). One unit of protein kinase activity is defined as 1 nmole of $^{33}$P transferred from [$\gamma^{33}$P] ATP to the substrate protein/minute/mg of protein at 37° C. The compounds of formula I here show IC$_{50}$ values in the range between 0.005 and 20 µM, especially between 0.01 and 1 µM.

VEGF-R1 inhibition can be shown as follows: the test is conducted using Flt-1 VEGF-receptor tyrosine kinase. The detailed procedure is as follows: 30 µl kinase solution (kinase domain of Flt-1, Shibuya et al., Oncogene 5, 519-24 [1990], according to the specific activity, in order to achieve an activity of 4000-6000 counts per minute [cpm] in the sample without inhibitor) in 20 mM Tris.HCl pH 7.5, 3 mM manganese dichloride (MnCl$_2$), 3 mM magnesium chloride (MgCl$_2$) and 3 µg/ml poly(Glu,Tyr) 4:1 (Sigma, Buchs, Switzerland), 8 µM [$^{33}$P]-ATP (0.2 µCi/batch), 1% dimethyl sulfoxide, and 0 to 50 µM of the compound to be tested are incubated together for 10 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid (H$_3$PO$_4$), incubated for 10 minutes each time while shaking, then mounted in a Hewlett Packard TopCount Manifold and the radioactivity measured after the addition of 10 µl Microscint® (β-scintillation counter liquid; Packard USA). IC$_{50}$-values are determined by linear regression analysis of the percentages for the inhibition of each compound in three concentrations (as a rule 0.01, 0.1, and 1 µM). The IC$_{50}$ values that can be found with the compounds of formula I are in the range of 0.001 to 100 µM, especially in the range from 0.01 to 20 µM.

Analogously to the above test, the efficacy of the compounds according to the invention as inhibitors of VEGF-R2 tyrosine kinase activity can be tested using the VEGF receptor tyrosine kinase KDR. In this test, instead of the Flt-1 kinase domain, the KDR kinase domain (Parast et al., Biochemistry 37 (47), 16788-801 (1998)) is used. The only difference in carrying out this test from the above test lies in the concentration of poly(Glu,Tyr) 4:1 (8 µg/ml), MnCl$_2$ (1 mM) and MgCl$_2$ (10 mM). Compounds of formula I in this instance have IC$_{50}$ values in the range of 0.001 µM to 20 µM, preferred compounds especially in the range of 1 nM to 500 nM.

The inhibition of VEGF-induced receptor autophosphorylation can be confirmed with an in vitro experiments in cells such as transfected CHO cells, which permanently express human VEGF-R2 (KDR), are seeded in complete culture medium (with 10% fetal calf serum=FCS) in 6-well cell-culture plates and incubated at 37° C. under 5% CO$_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20° (polyoxyethylen(20)sorbitane monolaurate, ICI/Uniquema) (PBST). The cell lysates (20 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition). The compounds of formula I here show an $IC_{50}$ in the range of 0.001 to 20 μM, preferred compounds especially between 0.001 and 0.5 μM.

Based on the property of the compounds of formula I as potent VEGF receptor inhibitors, the compounds of formula I are especially suitable for the treatment of diseases associated with deregulated angiogenesis, especially diseases caused by ocular neovascularisation, especially retinopathies such as diabetic retinopathy or age-related macula degeneration, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, including rheumatoid arthritis, fibrotic disorders (e.g. hepatic cirrhosis), diabetes, endometriosis, chronic asthma, arterial or post-transplantational atherosclerosis, neurodegenerative disorders, e.g. multiple sclerosis, and especially neoplastic diseases such as cancer (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of formula I is especially suited also to preventing the metastatic spread of tumours and the growth of micrometastases. The compounds of the formula I, due to their activity as kinases, are also useful in treatment in connection with transplantation.

With the groups of preferred compounds of formula I mentioned hereinafter, definitions of substituents from the general definitions mentioned hereinbefore may reasonably be used, for example, to replace one or more up to all more general definitions with more specific definitions or especially with definitions characterized as being preferred.

Compounds of formula I are prepared analogously to methods that, for other compounds, are in principle known in the art, but are novel when applied in the manufacture of the compounds of the present invention, and are especially prepared according to the methods described hereinbelow under 'Examples' or by analogous methods.

For example, a compound of the formula I can be prepared by reacting a) for the manufacture of a compound of the formula I wherein Y is O and the other moieties are as defined for a compound of the formula I, a hydroxyl compound of the formula II,

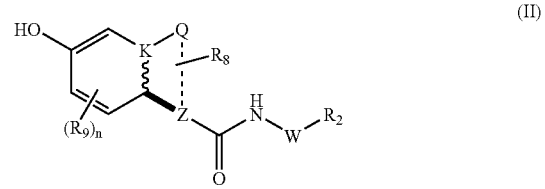

wherein K, Q, Z, W, $R_2$, $R_8$, $R_9$, n, the bond indicated by a waved line, the bond indicated by the broken line and the bond represented in bold have the meanings given under formula I, with a halo compound of the formula III,

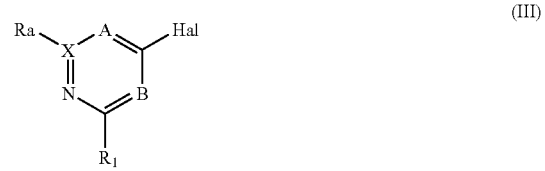

wherein $R_1$, X, A and B are as defined for a compound of the formula I, Hal is halo, especially chloro or bromo, and Ra is only present if X is not nitrogen (thus forming C-Ra) and is hydrogen or halo, especially chloro or bromo, and if Ra is halo reducing with hydrogen in the presence of a noble metal catalyst to hydrogen;

or b) a carbonic acid of the formula IV,

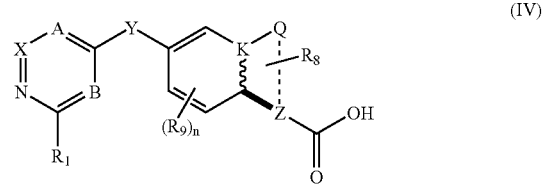

or a reactive derivative thereof, wherein X, A, B, $R_1$, $R_8$, $R_9$, n, K, Q, Y, Z, the bond indicated by the waved line, the bond indicated by the broken line and the bold bond are as defined under formula I, with an amino compound of the formula V,

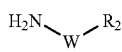 (V)

wherein W and $R_2$ are as defined for a compound of the formula I;

and, if desired, transforming a compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers.

The reaction under a) preferably takes place in the presence of an appropriate solvent and a base, e.g. in N-methylpyrrolidine in the presence of an alkaline metal phosphate, such as potassium phosphate, for example at temperatures from 0° C. to the reflux temperature of the corresponding reaction mixture.

The reduction of halo Ra into hydrogen, if Ra is hydrogen, then subsequently takes place e.g. by hydrogenation in the presence of a noble metal catalyst, such as palladium or platinum, preferably on a carrier, such as coal, in an appropriate solvent, such as water, tetrahydrofurane or mixtures thereof, and a tertiary nitrogen base, such as tri-lower alkylamine, e.g. trieathylamine, for example at temperatures from 0° C. to the reflux temperature of the corresponding reaction mixture.

The amide bond formation under b) preferably takes place, if the reactive derivative of the carbonic acid of the formula IV is a lower alkyl ester (with CO—O-lower alkyl instead of the carboxy group), e.g. by Lewis acid mediated N-acylation by first adding a Lewis acid, especially a tri-lower alkylaluminium, such as trimethylaluminium, to the amine of the formula V, e.g. in an appropriate solvent such as toluene, e.g. at temperatures from 0 to 30° C., and then adding the lower alkyl ester of the formula IV, if desired, in another solvent, such as tetrahydrofurane, and heating, e.g. to a temperature from 30 to 120° C.; or, if the reactive derivative is a carbonic acid halogenide (with a group CO-Hal, wherein Hal is halo, preferably chloro or bromo, instead of the carboxy group in formula IV; obtainable e.g. by reacting the free carbonic acid of the formula IV with oxalyl chloride in an appropriate solvent, such as methylene chloride, e.g. at temperatures in the range from 0 to 50° C.) in an appropriate solvent, such as methylene chloride, e.g. at temperatures from 0 to 50° C.; or by forming the reactive derivative of the carbonic acid of the formula IV in situ using customary condensation reagents, such as HBTU, HAT or the like.

A compound of the formula IA may be converted into a different compounds of the formula I.

For example, a compound of the formula I wherein $R_1$ is amino or —$C_1$-$C_7$—$NH_2$ can be alkylated or acylated to a compound of the formula I wherein $R_1$ is —$C_0$-$C_7$—$NR_4R_5$ wherein at least one of $R_4$ and $R_5$ is unsubstituted or substituted lower alkyl (e.g. by reacting with appropriate unsubstituted or substituted lower alkylhalogenides or -toluenesulfates; or by acylating with a corresponding acyl halogenide, such as lower alkyl-chloroformiate, in the presence of an appropriate solvent and/or a tertiary nitrogen base, such as pyridine, e.g. at temperatures in the range from 0 to 50° C.).

By analogous reactions, a compound of the formula I wherein $R_1$ is —$C_0$-$C_7$—$R_3$, wherein $R_3$ is is unsubstituted or substituted lower alkyl or unsubstituted or substituted alkylcarbonyl, can be obtained by alkylation or acylation with a corresponding unsubstituted or substituted alkylhalogenide or alkylcarbonyl-halogenide, respectively.

A compound of the formula I wherein $R_1$ is halo, e.g. chloro or bromo, can be converted to the corresponding compound of the formula I wherein $R_1$ is $NR_4R_5$ by reaction with an amine of the formula H—$NR_4R_5$, e.g. in the presence of an appropriate solvent, such as tetrahydrofurane, e.g. at temperatures in the range from 0 to 50° C.

A compound of the formula I wherein $R_1$ is cyano (obtainable e.g. from a corresponding compound of the formula I wherein $R_1$ is halo by reaction in an appropriate solvent, e.g. DMSO and/or water, 1,4-diazobicyclo[2,2,2]octan and an alkaline metal cyanide, e.g. KCN, e.g. by reaction at temperatures in the range from 10 to 70° C.) can, for example be converted into the corresponding compound wherein $R_1$ is —$C_1$—$NR_4R_5$ (wherein $R_4$ and $R_5$ are as defined above) by first converting into the $R_1$=—$CH_2$—$NH_2$ compound of the formula I, e.g. in the presence of an appropriate solvent, such as THF, and aqueous $NH_3$ (e.g. 25%) by hydrogenation in the presence of a hydrogenation catalyst, e.g. Raney-Nickel, and then acylating or alkylating the amino compound to introduce the corresponding $R_4$ and/or $R_5$ moiety or moieties other than hydrogen (e.g. by using compounds of the formula $R_4$-Hal and/or $R_5$-Hal wherein $R_4$ and $R_5$ are as defined under formula I and Hal is halogen, e.g. chloro or bromo. .

A halo $R_1$ may be converted into a group —C(=O)—OH, e.g. by reacting a corresponding halo compound of the formula I in the presence of a tertiary nitrogen base, e.g. triethylamine, a catalyst such as $PdCl_2[P(C_6H_5)_3]_2$, and an alcohol falling under the formula $R_6H$ wherein $R_6$ is lower alkoxy which is unsubstituted or substituted, such as ethanol, under a CO-atmosphere at elevated pressure (e.g. of 100 to 140 bar in an autoclave) to the corresponding $R_1$=C(=O)—$R_6$ compound. This can e.g. be converted into the corresponding compound wherein $R_6$ is hydroxy by hydrolysis, e.g. in the presence of a base such as lithium hydroxide in water and/or an appropriate organic solvent, such as tetrahydrofurane. If desired, unsubstituted or substituted amino can be introduced into the obtainable $R_1$=COOH compound by condensation with the corresponding amine $R_6$—H wherein $R_6$ is unsubstituted or mono- or di-substituted amino, e.g. employing a lithium salt of the carboxy $R_1$ compound, a tertiary nitrogen base, such as triethylamine, 4-dimethylamino-pyridine, an appropriate solvent such as dimethylformamide and a condensation agent, e.g. propylphosphonic anhydride.

A compound of the formula I wherein $R_1$ is methyl can be converted to a compound of the formula I wherein $R_1$ is —$CH_2$—$OR_3$ wherein $R_3$ is as defined for a compound of the formula I, especially lower alkyl, by first converting it into a compound of the formula I* wherein instead of $R_1$ Halo-$CH_2$— is present, e.g. bromomethyl, for example by reacting the methyl compound with N-bromosuccinimide and α,α-azobisisobutyronitrile in an appropriate solvent, such as chloroform, at elevated temperatures, e.g. 80° C., in the presence of strong light, and then converting the bromomethyl in the compound of the formula I* by reaction with an alcoholate compound of the formula $R_3$—O-Met wherein Met is an alkaline metal, e.g. Na, in the presence of a corresponding alcohol $R_3$—OH into the corresponding compound of the formula I wherein $R_1$ is —$CH_2$—$OR_3$.

Salts of compounds of formula I having at least one salt-forming group may be prepared in a manner known per se. For example, an acid addition salt of compounds of formula I with basic groups (e.g. basic nitrogen) can be obtained in customary manner, e.g. by treating a compound of the formula I with an acid or a suitable anion exchange reagent. A salt of a compound of formula I having acid groups may be formed by treating the compound with a metal compound, such as an alkali metal salt of a suitable organic carboxylic acid, e.g. the sodium salt of 2-ethylhexanoic acid, with an organic alkali metal or alkaline earth metal compound, such as the corresponding hydroxide, carbonate or hydrogen carbonate, such as sodium or potassium hydroxide, carbonate or hydrogen carbonate, with a corresponding calcium compound or with ammonia or a suitable organic amine, stoichiometric amounts or only a small excess of the salt-forming agent preferably being used. Internal salts of compounds of formula I containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

A salt of a compound of the formula I (=compound of the invention) can be converted in customary manner into the free compound; a metal or ammonium salt can be converted, for example, by treatment with a suitable acid, and an acid addition salt, for example, by treatment with a suitable basic agent into a different salt. In both cases, suitable ion exchangers may be used.

Stereoisomeric mixtures of a compound of the formula I, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999. Corresponding protecting groups can be introduced, used and removed at appropriate stages at any stage in the manufacture of a compound of the formula I.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Intermediates and final products can be worked up and/or purified according to standard methods, e.g. using chromatographic methods, distribution methods, (re-) crystallization, and the like.

Starting materials and intermediates (both in each case including salts thereof), especially of the formulae II, III, IV and V, can be prepared in analogy to the methods described in the Examples or in the reference examples, according to or in analogy to methods that are known in the art and/or they are commercially available.

Starting materials can, for example, preferably be prepared as follows:

Where in the starting materials and intermediates $R_1$, $R_2$, $R_3$, $R_4$, $R_5$, $R_6$, $R_7$, $R_8$, $R_9$, A, B, X, Y, Z, W, K, Q, n, a bond indicated by a waved line, a bond indicated by a broken line and/or a bond represented in bold, these symbols preferably have the meanings given for a compound of the formula I, if not indicated otherwise.

The starting materials used in the preparation of the compounds of formula I are known, capable of being prepared according to known processes, or commercially obtainable. In particular, the anilines to be used as starting material in the preparation of the compounds of formula I can be prepared as described in WO 03/099771, WO 05/051366 or by analogy thereto, are commercially available or can be prepared according to known processes. Starting materials and appropriate manufacturing methods can also be deduced from copending patent application PCT/IB2005/004030 published on Jun. 8$^{th}$, 2006 under WO2006/059234 which is here, especially regarding such materials and manufacturing methods, incorporated by reference, as well as from the reference examples from that application.

A compound of the formula IIC,

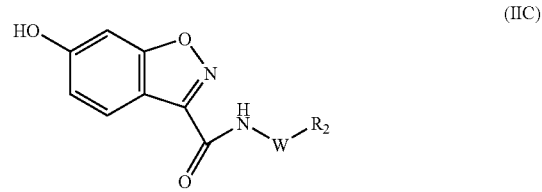

(IIC)

(appropriate e.g. for the manufacture of a compound of the formula IC given above wherein Y is O) which is an embodiment of a compound of the formula II, can for example be obtained by reacting 1,3-6-hydroxy-benzo[d]isoxazole-3-carboxylic acid ethyl ester (obtainable e.g. according to J. Am. Chem. Soc. 97 (1974), 7305) to the corresponding benzyloxy compound as shown below in Example 1, step 1.1. The 6-benzyloxy-benzo[d]isoxazole-3-carboxylic acid ethyl ester can then, by or in analogy to the procedure given in Example 1, Step 1.2, be reacted with an amino compound of the formula V as defined above, followed by removal of the 6-benzyl protection group by catalytic hydrogenation e.g. as described in Example 1 Step 1.3. Thus the compound of the formula IIC is obtained.

In analogy to this, a compound of the formula IID,

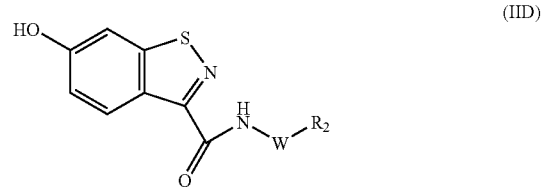

(IID)

(appropriate e.g. for the manufacture of a compound of the formula ID given above wherein Y is O) which is an embodiment of a compound of the formula II can be obtained from 6-methoxy-benzo[d]isothiazole-3-carboxylic acid (see Example 6 Step 6.1) by reaction with a compound of the formula V as given above by or in analogy to the reaction given in Step 20.6 to the corresponding amide from which then the methyl of the 6-methoxy group can be cleaved off by or in analogy to the method described in Step 6.2 with $BBr_3$ in methylene chloride, yielding a corresponding compound of the formula IID.

Compounds of the formula IIA,

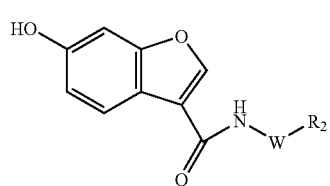

(IIA)

(appropriate e.g. for the manufacture of a compound of the formula IA given above wherein Y is O, an embodiment of a compound of the formula II) can, for example, be prepared from 6-hydroxy-benzofuran-3-carboxylic acid methyl ester (see Example 9 Step 9.4) followed by reaction with a compound of the formula V as described above under reaction conditions analogous to those described in Example 9 to give corresponding compounds of the formula IIA.

Compounds of the formula IIB,

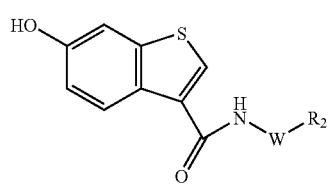

(IIB)

(appropriate e.g. for the manufacture of a compound of the formula IB given above wherein Y is O, an embodiment of a compound of the formula II) can, for example, be prepared from 6-hydroxy-benzothiophene-3-carboxylic acid methyl ester (see Example 12 Step 12.3) followed by reaction with a compound of the formula V as described above under reaction conditions as described or analogous to those described in Example 26.4 and if required 26.5 to give corresponding compounds of the formula IB.

Compounds of the formula III are commercially available, can be produced according to methods that are known in the art and/or are known in the art.

Compounds of the formula IV, or reactive carbonic acid derivatives thereof, can be prepared, for example, as follows:

A compound of the formula VI,

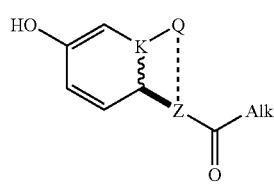

(VI)

wherein the symbols K, Q and Z and the waved, the broken and the bold bond have the meanings given for a compound of the formula I and Alk is lower alkyl, can be prepared, for example, as given in the examples. For example, some representative starting materials of the formula VI can be prepared as follows: 1, 3-6-hydroxy-benzo[d]isoxazole-3-carboxylic acid ethyl ester (an embodiment of a compound of the formula VI) as a starting material for a compound of the formula IC can be obtained e.g. according to J. Am. Chem. Soc. 97 (1974), 7305; 6-hydroxy-benzo[d]isothiazole-3-carboxylic acid lower alkyl ester as a starting material for a compound of the formula ID can be obtained from 6-methoxy-benzo[d]isothiazole-3-carboxylic acid (see Example 6, Step 6.1) by esterification with a lower alkanol according to standard procedures and conversion of the 6-methoxy-group in the obtainable product under analogous conditions as described in Example 6 Step 6.2; 6-hydroxy-benzofuran-3-carboxylic acid methyl ester as a further embodiment of a compound of the formula VI (see Example 9 Step 9.4) can serve as a starting material for a compound of the formula IA. 6-Hydroxy-benzothiophene-3-carboxylic acid methyl ester (see Example 12 Step 12.3) as a further embodiment of a compound of the formula VI can serve as a starting material for a compound of the formula IB. 6-Hydroxypyrazolo[1,5-a]pyridine-3-carboxylic acid methyl ester (see example 15 Step 15.6) can serve as starting material for a compound of the formula IE, e.g. by removal. Corresponding compounds of the formula VI wherein $R_8$ and one or more substituents $R_9$ (n=1, 2 or 3) are present can be prepared by analogous methods using the corresponding starting materials and reagents. The esters of the formula VI can be used directly in the process of process variant b) given above or converted into free carbonic acids.

The corresponding compounds to those of the formulae IIA, IIB, IIC, IID and IIE wherein substitutents $R_9$ (n=1, 2 or 3) and/or $R_8$ are present can be prepared in analogy to those of formula IIA to IIE.

In order to manufacture a corresponding compound of the formula IV, a compound of the formula VI can then be reacted with a compound of the formula III as defined above under reaction conditions as defined for process a) given above (reaction of a compound of the formula VI instead of a compound of the formula II given there with a compound of the formula II).

Compounds wherein OH in the formulae IV obtainable as just described is instead SH can be obtained by using the appropriate S- instead of O-comprising starting materials, e.g. as described in example 12 Step 12.1. Y=S in a compound of the formula II (or of the formula I, then being another conversion reaction) can be oxidised to S(=O) (sulfinyl) or S(=O)$_2$ (sulfonyl) e.g. as described in Ref.-Example 59 (with $H_2O_2$) or Ref.-Example 60 (with $KMnO_4$ in the presence of acetic acid). They can be used in an alternative process for the manufacture of a compound of the formula I wherein Y is S, SO or SO$_2$, respectively.

Amino compounds of the formula V are known in the art or can be prepared as described in the Examples and/or reference examples.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula IA is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosauren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula IA described as being preferred. The invention also relates to novel intermediates and/or starting materials. Special preference is given to reaction conditions and novel intermediates that are identical or analogous to those mentioned in the Examples.

Pharmaceutical Methods, Preparations and the Like

The invention relates also to pharmaceutical compositions comprising a compound of formula I, to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment of (this, in a broader aspect of the invention, also includes the prevention of (=prophylaxis against)) a disease that responds to inhibition of protein kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula I according to the invention, or a tautomer thereof or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilizing, mixing, granulating or confectioning processes.

A compound of the formula I may also be used to advantage in combination with other anti-proliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R. P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:

a) compounds targeting, decreasing or inhibiting the activity of the fibroblast growth factor-receptors (FGF-Rs);
b) compounds targeting, decreasing or inhibiting the activity of the insulin-like growth factor I receptor (IGF-IR), especially compounds which inhibit the IGF-IR, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C(PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; llmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor);
g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzene-malonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxy-phenyl) methyl]amino}-benzoic acid adamantyl ester; NSC 680410, adaphostin); and
h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or any combination thereof.

Preferred compounds of the formula I (which are also preferred for pharmaceutical compositions, methods and uses according to the invention), tautomers and/or salts thereof can be deduced from the dependent claims which are incorporated here by reference.

The invention relates especially to compounds of the formula I as given in the examples, tautomers thereof and/or pharmaceutically acceptable salts thereof.

The following Examples serve to illustrate the invention without limiting the scope thereof.

EXAMPLES

Temperatures are measured in degrees Celsius. Unless otherwise indicated, the reactions take place at room temperature under $N_2$-atmosphere.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

Abbreviations

| | |
|---|---|
| Anal. | elemental analysis (for indicated atoms, difference between calculated and measured value ≦ 0.4%) |
| aq. | aqueous |
| brine | saturated solution of NaCl in water |
| celite | Celite ® (filtering aid based on diatomaceous earth; Celite Corporation, Lompoc, USA) |
| conc. | concentrated |
| DIPE | diisopropyl-ether |

-continued

| | |
|---|---|
| DMAP | dimethylaminopyridine |
| DMEU | 1,3-dimethyl-2-imidazolidinone |
| DMF | dimethyl formamide |
| DMSO | dimethyl sulfoxide |
| ether | diethylether |
| Et$_3$N | triethylamine |
| EtOAc | ethyl acetate |
| EtOH | ethanol |
| eq. | equivalent |
| Ex. | Example |
| h | hour(s) |
| HPLC | high pressure liquid chromatography |
| Hyflo | Hyflo Super Cel ® (filtering aid based on diatomaceous earth; obtainable from Fluka, Buchs, Switzerland) |
| HV | high vacuum |
| l | liter(s) |
| Me | methyl |
| MeOH | methanol |
| min | minute(s) |
| m.p. | melting point |
| MPLC | medium pressure liquid chromatography Combi Flash system: Systeme: Combi Flash Companion from Isco, Inc.; Columns: RediSep ® flash column, Teledyne Isco, filled with 4 g, 12 g, 40 g or 120 g of SiO$_2$; application to column: either mixture is dissolved as a concentrated solution in eluent, or a solution of the mixture is concentrated together with SiO$_2$ in vacuo and applied as powder) Gilson system: reversed phase Nucleosil C18 (H$_2$O/CH$_3$CN + TFA), generally product obtained as free base after neutralization with NaHCO$_3$ |
| MS | mass spectrum |
| NMP | N-methyl-pyrrolidone |
| Ph | phenyl |
| propylphos-phonic anhydride: | 2,4,6-tripropyl-1,3,5,2,4,6-trioxatripho-phorinane-2,4,6-trioxide [68957-94-8]; 50 % in DMF |
| R$_f$ | ratio of fronts (TLC) |
| rt | room temperature |
| sat. | saturated |
| THF | tetrahydrofuran (distilled from Na/benzophenone) |
| TFA | trifluoroacetic acid |
| TLC | thin layer chromatography |
| t$_{Ret}$ | retention time (HPLC) |

HPLC Conditions:

Linear gradient 20-100% CH$_3$CN (0.1% TFA) and H$_2$O (0.1% TFA) in 13 min+5 min 100% CH$_3$CN (0.1% TFA); detection at 215 nm, flow rate 1 ml/min at 25 or 30° C. Column: Nucleosil 120-3 C18 (125×3.0 mm).

Anilines used as educts: Most respective anilines are either commercially available or described in WO 03/099771, WO 05/051366 or WO 05/063720 or can be prepared analogously to the therein exemplified derivatives.

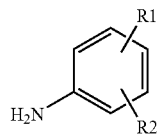

Example 1

6-(2-Chloro-pyrimidin-4-yloxy)-benzo[d]isoxazole-3-carboxylic acid (3-trifluoromethyl-phenyl)-amide

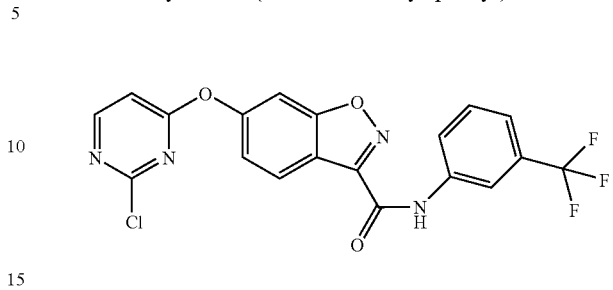

A mixture of 294 mg (0.91 mMol) 6-hydroxy-benzo[d]isoxazole-3-carboxylic acid (3-trifluoromethyl-phenyl)-amide (Step 1.3), 149 mg (1.00 mMol) 2,4-dichlorpyrimidine and 426 mg (2.0 mMol) K$_3$PO$_4$ in 5 ml NMP is stirred for 20 h at rt. The reaction mixture is diluted with CH$_2$Cl$_2$ and 5% citric acid in water, the aq. phase separated off and extracted with CH$_2$Cl$_2$. The organic layers are washed with water and brine, dried (Na$_2$SO$_4$) and concentrated. Column chromatography (SiO$_2$; CH$_2$Cl$_2$→CH$_2$Cl$_2$/EtOAc 99:1) gives the title compound: MS: [M+1]$^+$=435; TLC(CH$_2$Cl$_2$/EtOAc 49:1): R$_f$=0.66.

The starting material is prepared as follows:

Step 1.1:
6-Benzyloxy-benzo[d]isoxazole-3-carboxylic acid ethyl ester

To a solution of 0.98 g (4.73 mMol) 6-hydroxy-benzo[d]isoxazole-3-carboxylic acid ethyl ester [preparation see: *J. Am. Chem. Soc.* 97 (1974), 7305] in 100 ml acetone, 545 µl (4.73 mMol) benzylchloride, 3.08 g (9.46 mMol) Cs$_2$CO$_3$ und 10 mg NaI are added. Then the mixture is stirred for 2 h at rt and 5 h at 56° C. The reaction mixture is diluted with EtOAc and water, the aq. phase separated off and extracted with EtOAc. The organic layers are washed with water and brine, dried (Na$_2$SO$_4$) and concentrated after addition of 10 g SiO$_2$. The resulting powder is put on top of a chromatography column (SiO$_2$) and the title compound eluated with hexan/EtOAc 9:1→8:2→7:3: MS: [M+1]$^+$=298; TLC(hexane/EtOAc 3:1): R$_f$=0.54.

Step 1.2:
6-Benzyloxy-benzo[d]isoxazole-3-carboxylic acid (3-trifluoromethyl-phenyl)-amide In a dried vessel, 99 µl (0.79 mMol) 3-trifluoromethyl-aniline are dissolved in 14 ml toluene and cooled to 10° C. Then 1.2 ml Me$_3$Al (2 M in toluene; 2.4 mMol) are added via syringe. After 1 h at rt, a solution of 236 mg (0.79 mMol) 6-benzyloxy-benzo[d]isoxazole-3-carboxylic acid ethyl ester in 3 ml THF is added and the reaction mixture stirred for 25 min in an oil bath at 110° C. The solution is cooled in ice and hydrolyzed with 30 ml of a sat. NH$_4$Cl. After 15 min stirring, EtOAc and Celite are added. The mixture is filtered through Celite, the solid washed with EtOAc and water, the aq. phase separated from the filtrate and extracted with EtOAc. The organic layers are washed with water and brine, dried (Na$_2$SO$_4$) and concentrated. Crystallisation from EtOAc/hexane gives the title compound: MS: [M−1]=411; TLC(hexane/EtOAc 3:1): R$_f$=0.51.

Step 1.3: 6-Hydroxy-benzo[d]isoxazole-3-carboxylic acid (3-trifluoromethyl-phenyl)-amide Hydrogenation of 202 mg (0.49 mMol) 6-benzyloxy-benzo[d]isoxazole-3-carboxylic acid (3-trifluoromethyl-phenyl)-amide dissolved in 6 ml THF in presence of 70 mg Pd/C (10%, Engelhard 4505), filtration, concentration of the filtrate and trituration from hexane gives the title compound: MS: [M−1]=321; TLC(hexane/EtOAc 1:1): R$_f$=0.51.

Alternative Method:

Step 1.1*: 6-Triisopropylsilanyloxy-benzo[d]isoxazole-3-carboxylic acid ethyl ester To a solution of 0.80 g (3.86 mMol) 6-hydroxy-benzo[d]isoxazole-3-carboxylic acid ethyl ester [preparation see: *J. Am. Chem. Soc.* 97 (1974), 7305] in 8 ml DMF, 1.16 g (17 mMol) imidazol and 2.15 ml chlortriisopropylsilane (95%; 9.7 mMol) are added. After 50 min, the mixture is poured into ice-water and extracted twice with EtOAc. The organic phases are washed with 10% citric acid solution, 2× water and brine, dried (Na$_2$SO$_4$) and concentrated. Column chromatography (SiO$_2$; hexane/EtOAc 29:1) gives the title compound: MS: [M+1]$^+$=364; TLC(hexane/EtOAc 9:1): R$_f$=0.5.

Step 1.2*: 6-Triisopropylsilanyloxy-benzo[d]isoxazole-3-carboxylic acid (3-trifluoromethyl-phenyl)-amide In a dried vessel, 207 µl (1.66 mMol) 3-trifluoromethyl-aniline are dissolved in 28 ml toluene and cooled to 10° C. Then 2.5 ml Me$_3$Al (2 M in toluene; 5.0 mMol) are added via syringe. After 1 h at rt, a solution of 602 mg (1.66 mMol) 6-triisopropylsilanyloxy-benzo[d]isoxazole-3-carboxylic acid ethyl ester in 6 ml THF is added and the reaction mixture stirred for 30 min in an oil bath at 110° C. The solution is cooled in ice and hydrolyzed with 70 ml of a sat. NH$_4$Cl. After 15 min stirring, EtOAc and Celite are added. The mixture is filtered through Celite, the solid washed with EtOAc and water, the aq. phase separated from the filtrate and extracted with EtOAc. The organic layers are washed with water and brine, dried (Na$_2$SO$_4$) and concentrated, yielding the title compound as an oil: MS: [M−1]=477; TLC(hexane/EtOAc 19:1): R$_f$=0.30.

Step 1.3*: 6-Hydroxy-benzo[d]isoxazole-3-carboxylic acid (3-trifluoromethyl-phenyl)-amide 5.5 ml of a 1 M solution of Bu$_4$NF in THF are added to a solution of 1.045 g (2.18 mMol) 6-triisopropylsilanyloxy-benzo[d]isoxazole-3-carboxylic acid (3-trifluoromethyl-phenyl)-amide dissolved in 25 ml THF. After 55 min, the solution is concentrated in vacuo, the residue redissolved in water and EtOAc, the aq. layer separated off and extracted twice with EtOAc. The organic layers are washed twice with water and brine, dried (Na$_2$SO$_4$) and concentrated. Trituration in hexane gives the title compound.

Example 2

6-(2-Hydrazino-pyrimidin-4-yloxy)-benzo[d]isoxazole-3-carboxylic acid (3-trifluoromethyl-phenyl)-amide

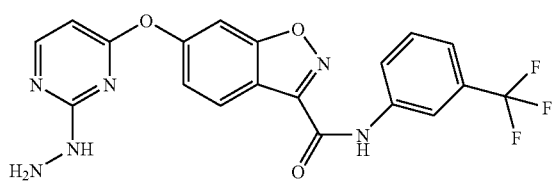

25 mg (0.058 mMol) 6-(2-chloro-pyrimidin-4-yloxy)-benzo[d]isoxazole-3-carboxylic acid (3-trifluoro-methyl-phenyl)-amide are dissolved in 2 ml THF. Then 9.2 µl (0.19 mMol) hydrazine hydrate are added in 3 portions over a period of 24 h giving the title compound: MS: [M+1]$^+$=431; HPLC: t$_{Ret}$=12.9.

Example 3

6-(2-Methylamino-pyrimidin-4-yloxy)-benzo[d]isoxazole-3-carboxylic acid (3-trifluoromethyl-phenyl)-amide

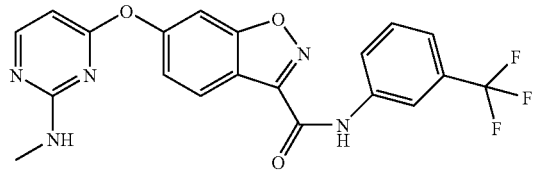

50 mg (0.115 mMol) 6-(2-chloro-pyrimidin-4-yloxy)-benzo[d]isoxazole-3-carboxylic acid (3-trifluoromethyl-phenyl)-amide are dissolved in 5 ml THF. Then 250 µl methylamine (2 M in THF; 0.50 mMol) are added and the solution is stirred in a sealed tube for 20 h. The mixture is diluted with water and EtOAc, the aq. layer separated off and extracted with EtOAc. The organic layers are washed with water and brine, dried (Na$_2$SO$_4$) and concentrated. Chromatography (reversed phase; Gilson) gives the title compound: MS: [M+1]$^+$=430; HPLC: t$_{Ret}$=14.0.

Example 4

6-(Pyrimidin-4-yloxy)-benzo[d]isoxazole-3-carboxylic acid (4-fluoro-3-trifluoromethyl-phenyl)-amide

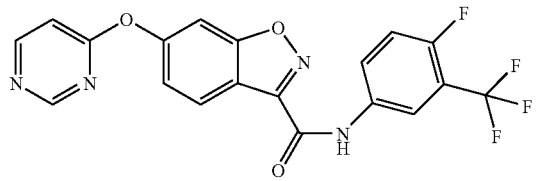

In a dried vessel, 46 µl (0.35 mMol) 4-fluoro-3-trifluoromethyl-aniline are dissolved in 6 ml toluene and cooled to 10° C. Then 550 µl Me$_3$Al (2 M in toluene; 1.1 mMol) are added via syringe. After 1 h at rt, a solution of 101 mg (0.35 mMol) 6-(pyrimidin-4-yloxy)-benzo[d]isoxazole-3-carboxylic acid ethyl ester in 1.25 ml THF is added and the reaction mixture stirred for 25 min in an oil bath at 110° C. Work up as described in step 1.2 gives the title compound: MS: [M−1]=419; Anal.: C,H,N,F.

The starting material is prepared as follows:

Step 4.1: 6-(2-Chloro-pyrimidin-4-yloxy)-benzo[d]isoxazole-3-carboxylic acid ethyl ester A suspension of 2.7 g (18.1 mMol) 2,4-dichloropyrimidine, 4.12 g (19.9 mMol) 6-hydroxy-benzo[d]isoxazole-3-carboxylic acid ethyl ester [preparation see: *J. Am. Chem. Soc.* 97 (1974), 7305] and 8.45 g (39.8 mMol) $K_3PO_4$ in 90 ml NMP is stirred for 22 h at rt. Then the mixture is diluted with 0.5 l $CH_2Cl_2$ and 0.9 l of a 5% citric acid solution. The organic phase is separated off, washed with water and brine, dried ($Na_2SO_4$) and concentrated. Column chromatography ($SiO_2$; $CH_2Cl_2$) gives the title compound: MS: $[M+1]^+$=320; TLC ($CH_2Cl_2$/EtOAc 49:1): $R_f$=0.42.

Step 4.2: 6-(Pyrimidin-4-yloxy)-benzo[d]isoxazole-3-carboxylic acid ethyl ester 300 mg (0.938 mMol) 6-(2-chloro-pyrimidin-4-yloxy)-benzo[d]isoxazole-3-carboxylic acid ethyl ester in 3 ml DMF and 262 µl (1.88 mMol) $Et_3N$ are hydrogenated in presence of 120 mg Pd/C (10%; Engelhard 4505). The catalyst is filtered off, the filtrate concentrated, the residue re-dissolved in EtOAc and water, the aq. layer separated off and extracted with EtOAc. The organic layers are washed with water and brine, dried ($Na_2SO_4$) and concentrated. Chromatography (Combi Flash; hexane/EtOAc 9:1→4:1) gives the title compound: MS: $[M+1]^+$=286; TLC(hexane/EtOAc 1:1): $R_f$=0.30.

Example 5

{4-[3-(3-Trifluoromethyl-phenylcarbamoyl)-benzo[d]isoxazol-6-yloxy]-pyrimidin-2-yl}-carbamic acid tert-butyl ester A & 6-(2-amino-pyrimidin-4-yloxy)-benzo[d]isoxazole-3-carboxylic acid (3-trifluoromethyl-phenyl)-amide B

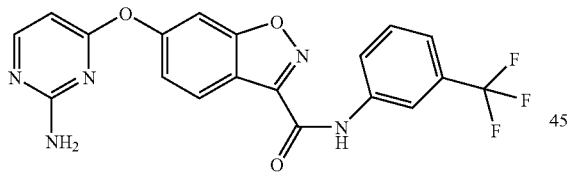

38 µl (0.30 mMol) 3-trifluoromethyl-aniline are dissolved in 6 ml toluene and cooled to 10° C. Then 0.46 ml $Me_3Al$ (2 M in toluene; 0.92 mMol) are added via syringe. After 1 h at rt, a solution of 121 mg (0.30 mMol) 6-(2-tert-butoxycarbonylamino-pyrimidin-4-yloxy)-benzo[d]isoxazole-3-carboxylic acid ethyl ester in 3 ml THF is added and the reaction mixture stirred for 20 min in an oil bath at 110° C. Workup as described in step 1.2, chromatography (Combi Flash; hexane/EtOAc 19:1→1:1) and reversed phase chromatography gives A and B. A: MS: $[M-1]^-$=514; B: MS: $[M+1]^+$=416.

The starting material is prepared as follows:

Step 5.1: 6-(2-tert-Butoxycarbonylamino-pyrimidin-4-yloxy)-benzo[d]isoxazole-3-carboxylic acid ethyl ester A solution of 1.4 g (4.3 mMol) 6-(2-chloro-pyrimidin-4-yloxy)-benzo[d]isoxazole-3-carboxylic acid ethyl ester (Step 4.1) in 32 ml dioxane is degassed repeatedly by evaporation and flushing with $N_2$. Then 2.1 g (6.44 mMol) $Cs_2CO_3$, 77 mg (0.13 mMol) 4,5-bis(diphenylphosphino)-9,9-dimethylxanthene, 39.3 mg (0.0429 mMol) tris(dibenzylidenaceton)dipalladium(0) and 603 mg (5.15 mMol) carbamic acid tert-butyl ester are added successively. After 4.5 h stirring at 110° C., the mixture is cooled to rt and another 77 mg 4,5-bis(diphenylphosphino)-9,9-dimethylxanthene, 39.7 mg tris(dibenzylidenaceton)dipalladium(0), 603 mg carbamic acid tert-butyl ester and 2.1 g $Cs_2CO_3$ are added and stirring is continued for 5 h. Then the cooled mixture is poured into EtOAc and water, the aq. layer separated off and extracted with EtOAc. The organic layers are washed with water and brine, dried ($Na_2SO_4$) and concentrated together with 8 g $SiO_2$. The resulting powder is put on top of a chromatography column ($SiO_2$; $CH_2Cl_2$) and the title compound eluted with $CH_2Cl_2$→$CH_2Cl_2$/EtOAc 4:1: MS: $[M+1]^+$=401; HPLC: $t_{Ret}$=15.4.

Example 6

6-(2-Amino-pyrimidin-4-yloxy)-benzo[d]isothiazole-3-carboxylic acid (4-fluoro-3-trifluoromethyl-phenyl)-amide

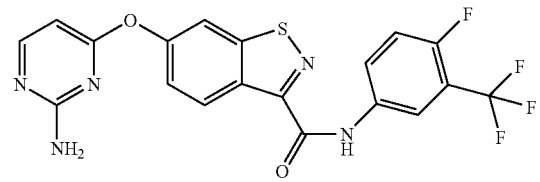

Hydrogenation of 51 mg (0.11 mMol) of 6-(2-amino-6-chloro-pyrimidin-4-yloxy)-benzo[d]isothiazole-3-carboxylic acid (4-fluoro-3-trifluoromethyl-phenyl)-amide (Step 6.3) in 10 ml THF and 46 µl (0.33 mMol) $Et_3N$ in presence of two portions of 0.1 g Pd/C (10%; Engelhard 4505) during 36 h, filtration, concentration of the filtrate and chromatography (Combi Flash; $CH_2Cl_2$/hexane 2:3→$CH_2Cl_2$→$CH_2Cl_2$/ether 7:3) gives the title compound: m.p.: 237-239° C.; MS: $[M+1]^+$=450.

The starting material is prepared as follows:

Step 6.1: 6-Methoxy-benzo[d]isothiazole-3-carboxylic acid (4-fluoro-3-trifluoromethyl-phenyl)-amide 209 mg (1.00 mMol) 6-methoxy-benzo[d]isothiazole-3-carboxylic acid (preparation see: WO 2004/029050, Procedure N), 269 mg (1.5 mMol) 4-fluoro-3-trifluoromethyl-aniline and 1.4 ml (10 mMol) $Et_3N$ are dissolved in 5 ml of dry DMF and cooled in an ice-bath. Then a solution of 1.17 ml (50% in DMF; 2.0 mMol) propylphosphonic anhydride is added. The mixture is stirred for 15 h at rt, when another 0.58 ml of propylphosphonic anhydride are added. After 2 h, the reaction mixture is poured into water and EtOAc, the aq. phase separated off and extracted twice with EtOAc. The organic layers are washed twice with water and brine, dried ($Na_2SO_4$) and partially concentrated. Addition of hexane precipitates the title compound: m.p.: 157° C.; MS: $[M+1]^+$=371.

Step 6.2: 6-Hydroxy-benzo[d]isothiazole-3-carboxylic acid (4-fluoro-3-trifluoromethyl-phenyl)-amide A suspension of 252 mg (0.68 mMol) 6-methoxy-benzo[d]isothiazole-3-carboxylic acid (4-fluoro-3-trifluoromethylphenyl)-amide in 15 ml CH₂Cl₂ is cooled in an ice-bath, then 20 ml of a 1 M solution of BBr₃ in CH₂Cl₂ are added. The suspension is stirred for 3 days at 45° C., the resulting solution is cooled, poured into water and EtOAc, the aq. layer is separated off and extracted twice with EtOAc. The organic layers are washed twice with water and sat. NaHCO₃, dried (Na₂SO₄) and concentrated. Chromatography (Combi Flash; acetone/hexane 1:95→2:3) gives the title compound: MS: [M−1]=355; TLC(hexane/acetone 2:1): R$_f$=0.46.

Step 6.3: 6-(2-Amino-6-chloro-pyrimidin-4-yloxy)-benzo[d]isothiazole-3-carboxylic acid (4-fluoro-3-trifluoromethyl-phenyl)-amide A mixture of 72 mg (0.44 mMol) 2-amino-4,6-dichloropyrimidine, 143 mg (0.40 mMol) 6-hydroxy-benzo[d]isothiazole-3-carboxylic acid (4-fluoro-3-trifluoromethyl-phenyl)-amide and 280 mg (1.32 mMol) K₃PO₄ in 2 ml NMP is stirred for 6 h at 70° C. Then the mixture is diluted with EtOAc and water, the aq. layer separated off and extracted twice with EtOAc. The organic phases are washed twice with water and brine, dried (Na₂SO₄) and concentrated. Chromatography (Combi Flash; CH₂Cl₂→CH₂Cl₂/EtOH 9:1) gives the title compound: MS: [M−1]=482/484; TLC(CH₂Cl₂): R$_f$=0.12.

Example 7

6-(2-Amino-pyrimidin-4-yloxy)-benzo[d]isothiazole-3-carboxylic acid [4-(4-methyl-piperazin-1-ylmethyl)-3-trifluoromethyl-phenyl]-amide

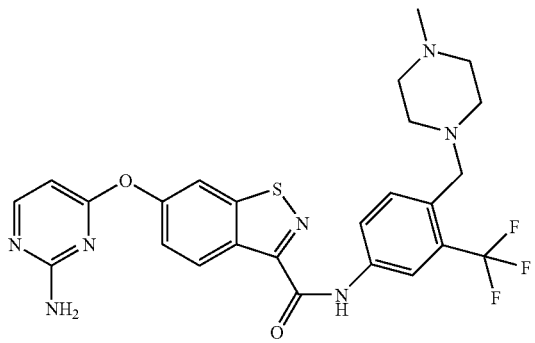

A solution of 296 mg (0.513 mMol) 6-(2-amino-6-chloro-pyrimidin-4-yloxy)-benzo[d]isothiazole-3-carboxylic acid [4-(4-methyl-piperazin-1-ylmethyl)-3-trifluoro-methyl-phenyl]-amide and 1.44 ml (10.3 mMol) Et₃N in 25 ml THF is hydrogenated in presence of 298 mg Pd/C 10%. To drive the reaction to completion, then the catalyst is filtered off, another portion of 298 mg Pd/C 10% is added and hydrogenation continued. The mixture is filtered through Celite, the filtrate diluted with a NaHCO₃ solution and EtOAc, the aq. layer separated off and extracted twice with EtOAc. The organic phases are washed twice with water and brine, dried (Na₂SO₄) and concentrated. Chromatography (Combi Flash; CH₂Cl₂/MeOH/$^{conc}$NH₃$^{aq}$ 95:4:1→90:10:1) gives the title compound: m.p.: 215-217° C.; MS: [M+1]⁺=544.

The starting material is prepared as follows:

Step 7.1: 6-Methoxy-benzo[d]isothiazole-3-carboxylic acid [4-(4-methyl-piperazin-1-ylmethyl)-3-trifluoromethyl-phenyl]-amide Prepared analogousely to step 6.1 from 2.0 g (9.57 mMol) 6-methoxy-benzo[d]isothiazole-3-carboxylic acid, 3.9 g (14.3 mMol) 4-(4-methyl-piperazin-1-ylmethyl)-3-trifluoromethyl-aniline, 13.3 ml (95.7 mMol) Et₃N and 11.17 ml (50% in DMF; 19.1 mMol) propylphosphonic anhydride in 100 ml of dry DMF: m.p.: 156° C.; MS: [M+1]⁺=465.

Step 7.2: 6-Hydroxy-benzo[d]isothiazole-3-carboxylic acid [4-(4-methyl-piperazin-1-ylmethyl)-3-trifluoromethyl-phenyl]-amide 1.923 g (4.14 mMol) 6-methoxy-benzo[d]isothiazole-3-carboxylic acid [4-(4-methyl-piperazin-1-ylmethyl)-3-trifluoromethyl-phenyl]-amide in 120 ml of a 1 M solution of BBr₃ in CH₂Cl₂ are stirred for 16 h at 45° C. Then the solution is poured into water and EtOAc, the aq. layer is neutralized with Na₂CO₃, separated off and extracted twice with EtOAc. The organic layers are washed twice with water and brine, dried (Na₂SO₄) and concentrated. Reversed phase chromatography (Gilson system) gives the title compound: MS: [M−1]=451; HPLC: t$_{Ret}$=11.6.

Step 7.3: 6-(2-Amino-6-chloro-pyrimidin-4-yloxy)-benzo[d]isothiazole-3-carboxylic acid [4-(4-methyl-piperazin-1-ylmethyl)-3-trifluoromethyl-phenyl]-amide Prepared as described in step 6.3 from 401 mg (2.45 mMol) 2-amino-4,6-dichloropyrimidine, 785 mg (1.74 mMol) 6-hydroxy-benzo[d]isothiazole-3-carboxylic acid [4-(4-methyl-piperazin-1-ylmethyl)-3-trifluoromethyl-phenyl]-amide and 1.5 g (7.1 mMol) K₃PO₄ in 45 ml NMP: MS: [M+1]⁺=578/580; HPLC: t$_{Ret}$=14.9.

Example 8

(4-{3-[4-(4-Methyl-piperazin-1-ylmethyl)-3-trifluoromethyl-phenylcarbamoyl]-benzo[d]isothiazol-6-yloxy}-pyrimidin-2-yl)-carbamic acid methyl ester

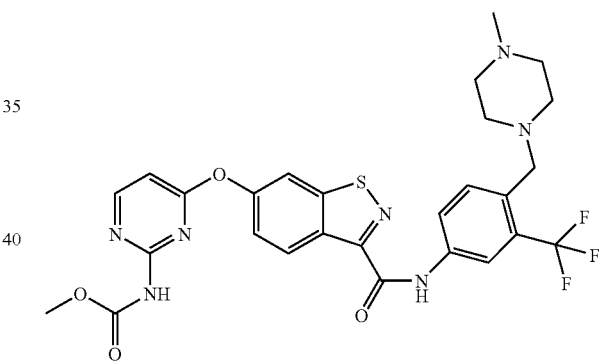

Can be prepared analogously as described in Ex. 11 from 6-(2-amino-pyrimidin-4-yloxy)-benzo[d]isothiazole-3-carboxylic acid [4-(4-methyl-piperazin-1-ylmethyl)-3-trifluoromethyl-phenyl]-amide (Ex. 7) and methylchloroformiate in CH₂Cl₂ and pyridine.

Example 9

6-(2-Amino-pyrimidin-4-yloxy)-benzofuran-3-carboxylic acid (4-fluoro-3-trifluoromethyl-phenyl)-amide

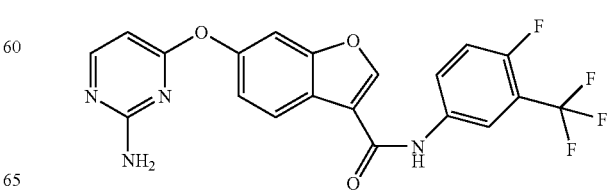

In a dried vessel, 108 mg (0.60 mMol) 4-fluoro-3-trifluoromethyl-aniline are dissolved in 10 ml toluene and cooled to 10° C. Then 900 μl Me$_3$Al (2 M in toluene; 1.8 mMol) are added via syringe. After 1 h at rt, a suspension of 171 mg (0.599 mMol) 6-(2-amino-pyrimidin-4-yloxy)-benzofuran-3-carboxylic acid methyl ester (Step 9.6) in 5 ml THF is added and the reaction mixture is stirred for 40 min in an oil bath of 110° C. The solution is cooled in ice and hydrolyzed with 20 ml of a sat. NH$_4$Cl. After 10 min stirring, the mixture is filtered through Celite, the solid washed extensively with EtOAc and water, the aq. phase separated from the filtrate and extracted with EtOAc. The organic layers are washed with water and brine, dried (Na$_2$SO$_4$) and concentrated. Column chromatography (SiO$_2$; EtOAc) and crystallization from EtOAc/hexane 1:1 gives the title compound: MS: [M+1]$^+$=433; TLC(hexane/EtOAc 1:9): R$_f$=0.22.

The starting material is prepared as follows:

Step 9.1: 6-Triisopropylsilanyloxy-benzofuran-3-one

To a solution of 9.8 g (65.3 mMol) 6-hydroxy-2H-benzofuran-3-one in 80 ml DMF, 10.6 g (157 mMol) imidazole and 16.6 ml (78.3 mMol) chloro-triisopropylsilane are added dropwise. After 1 h, the mixture is poured into 300 ml EtOAc and 300 ml water, the aq. phase is separated off and extracted with 3×100 ml EtOAc. The organic layers are washed 4 times with 10% citric acid solution, brine and dried (Na$_2$SO$_4$). Then char coal is added. Filtration, concentration and drying (10 mbar, 65-85° C.) give the oily title compound: MS: [M+1]$^+$=307; TLC(hexane/EtOAc 2:1): R$_f$=0.61.

Step 9.2: Trifluoro-methanesulfonic acid 6-triisopropylsilanyloxy-benzofuran-3-yl ester To an ice-cooled solution of 22.9 g (74.7 mMol) 6-triisopropylsilanyloxy-benzofuran-3-one in 300 ml CH$_2$Cl$_2$, 19.1 ml (164 mMol) 2,6-lutidine are added, followed dropwise by 17.6 ml (82.2 mMol) trifluormethanesulfonic acid anhydride. After 10 min, the mixture is warmed up to 15° C. for 20 min and then concentrated on the rotation-evaporator in vacuo. The residue is re-dissolved in CH$_2$Cl$_2$ and together with 100 g SiO$_2$ concentrated again. The resulting powder is put immediately on top of a chromatography column (hexane/EtOAc 99:1) and the title compound eluated with hexane/EtOAc 99:1 as an oil: MS: [M+1]$^+$=439; TLC(hexane/EtOAc 19:1): R$_f$=0.51.

Step 9.3: 6-Triisopropylsilanyloxy-benzofuran-3-carboxylic acid methyl ester A mixture of 256 mg (1.14 mMol) Pd(OAc)$_2$ and 517 mg (1.25 mMol) 1,3-bis-(diphenylphosphino)-propane in 96 ml DMF and 72 ml MeOH is stirred for 30 min under an Ar-atmosphere in an autoclave. Then 10 g (22.8 mMol) trifluoromethanesulfonic acid 6-triisopropylsilanyl-oxy-benzofuran-3-yl ester and 7 ml (50 mMol) Et$_3$N are added to the solution. The autoclave is sealed, a CO-atmosphere of 8 bar is applied, and the mixture is heated up to 70° C. for 5 h. After cooling to rt, the mixture is filtered through celite, the solide washed with MeOH and the filtrate concentrated in vacuo. The residue is re-dissolved in 400 ml EtOAc and washed with 4 portions of water and brine. The organic phase is dried (Na$_2$SO$_4$). Char coal is added, the mixture filtered and the filtrate concentrated. Column chromatography (SiO$_2$; CH$_2$Cl$_2$) gives the title compound as an oil: MS: [M+1]$^+$=349; TLC(hexane/EtOAc 19:1): R$_f$=0.33.

Step 9.4: 6-Hydroxy-benzofuran-3-carboxylic acid methyl ester 17.9 g (51.4 mMol) 6-Triisopropylsilanyloxy-benzofuran-3-carboxylic acid methyl ester are dissolved in 200 ml DMF. Then 34 g (108 mMol) tetrabutylammoniumfluorid trihydrate are added. After 30 min, the mixture is poured into 400 ml EtOAc and 600 ml water, the aq. phase is separated off and extracted 3 times with EtOAc. The organic layers are washed 4 times with water, brine and dried (Na$_2$SO$_4$). Then char coal is added and the mixture filtered. Partial concentration of the filtrate gives the crystalline title compound, which is filtered off and washed with ether and hexane: m.p.: 200-201° C. More product can be isolated from the filtrate by addition of 280 g SiO$_2$, concentration, application to a chromatography column (SiO$_2$; hexane/EtOAc 3: 1) and eluation with hexane/EtOAc 3:1.

Step 9.5: 6-(2-Amino-6-chloro-pyrimidin-4-yloxy)-benzofuran-3-carboxylic acid methyl ester A mixture of 6.20 g (32.3 mMol) 6-hydroxy-benzofuran-3-carboxylic acid methyl ester, 8.5 g (51.8 mMol) 2-amino-4,6-dichloropyrimidine and 14.2 g (67 mMol) K$_3$PO$_4$ in 250 ml NMP is stirred for 3.5 h at 60° C. Then the mixture is poured into 1 l EtOAc and 1 l water, the aq. layer separated off and extracted 3 times with EtOAc. The organic phases are washed with water and brine and dried (Na$_2$SO$_4$). Then char coal is added, the mixture filtered and the filtrate concentrated. Trituration from ether gives the title compound: m.p.: 213-214° C. More product can be obtained from the filtrate by column chromatography (SiO$_2$; hexane/EtOAc 2:1) as described in step 9.4.

Step 9.6: 6-(2-Amino-pyrimidin-4-yloxy)-benzofuran-3-carboxylic acid methyl ester A solution of 9.2 g (28.8 mMol) 6-(2-amino-6-chloro-pyrimidin-4-yloxy)-benzofuran-3-carboxylic acid methyl ester and 23.4 ml (0.29 Mol) pyridine in 1 l THF is hydrogenated in presence of 3.9 g Pd/C 10% during 5 h. The mixture is filtered through a pad of celite and char coal, the solid washed extensively with THF and MeOH and the filtrate concentrated. The residue is stirred with 400 ml EtOAc and 200 ml water. Filtration of the suspension and washing with water and EtOAc yields the title compound: m.p.: 194-196° C.; MS: [M+1]$^+$=286. The aq. layer is separated off from the filtrate and extracted 3 times with EtOAc. The organic phases are washed with water and brine, dried (Na$_2$SO$_4$) and concentrated. Trituration from ether and EtOAc yields more of the title compound.

Example 10
The following derivatives are obtained analogously to Ex. 9.
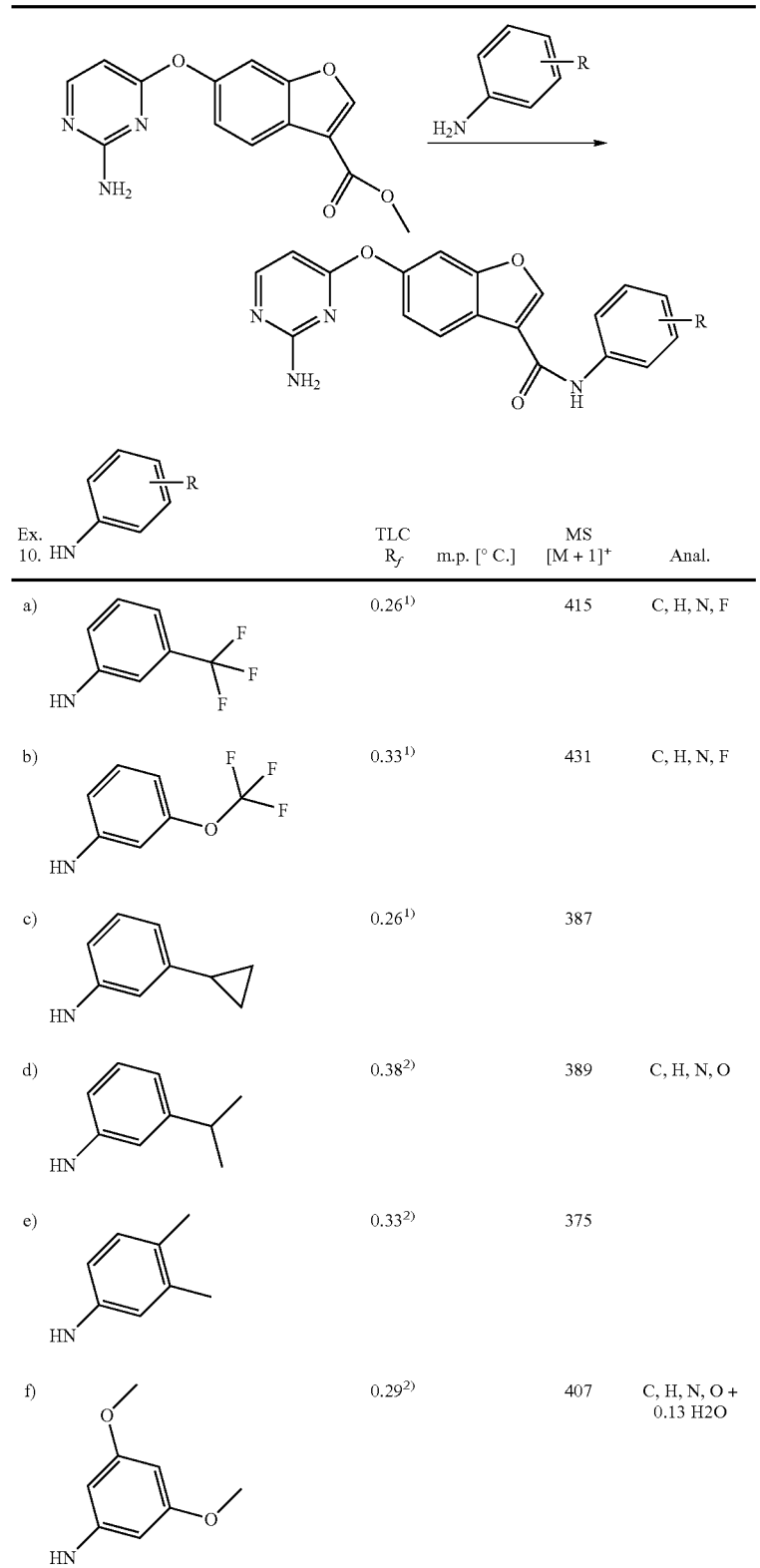
| Ex. 10. | HN-R | TLC $R_f$ | m.p. [° C.] | MS $[M+1]^+$ | Anal. |
|---|---|---|---|---|---|
| a) | 3-CF3-phenyl | 0.26[1] | | 415 | C, H, N, F |
| b) | 3-OCF3-phenyl | 0.33[1] | | 431 | C, H, N, F |
| c) | 3-cyclopropyl-phenyl | 0.26[1] | | 387 | |
| d) | 3-isopropyl-phenyl | 0.38[2] | | 389 | C, H, N, O |
| e) | 3,4-dimethyl-phenyl | 0.33[2] | | 375 | |
| f) | 3,5-dimethoxy-phenyl | 0.29[2] | | 407 | C, H, N, O + 0.13 H2O |

-continued
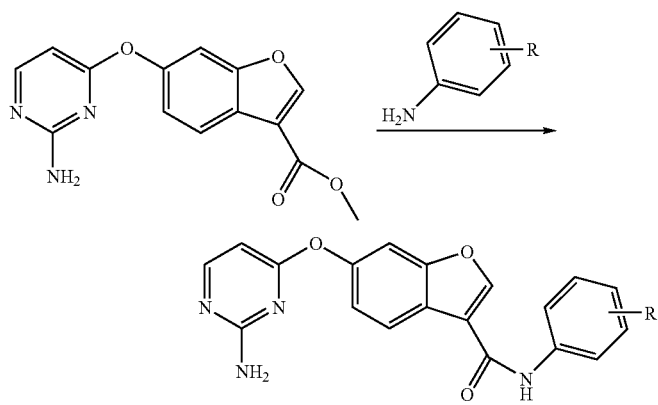
| Ex. 10. HN-R | TLC $R_f$ | m.p. [° C.] | MS $[M + 1]^+$ | Anal. |
|---|---|---|---|---|
| g)  | 0.37[2)] | | 429 | C, H, N, F, O |
| h)  | 0.36[2)] | | 403 | C, H, N, O |
| i)  | 0.34[2)] | | 439 | C, H, N, O |
| j)  | 0.36[3)] | 217-218 | 527 | C, H, N, F |
[1)]EtOAc/hexane 9:1;
[2)]EtOAc;
[3)]CH$_2$Cl$_2$/MeOH/$^{conc}$NH$_3^{aq}$-90:10:1

Example 11

(4-{3-[4-(4-Methyl-piperazin-1-ylmethyl)-3-trifluoromethyl-phenylcarbamoyl]-benzofuran-6-yloxy}-pyrimidin-2-yl)-carbamic acid methyl ester

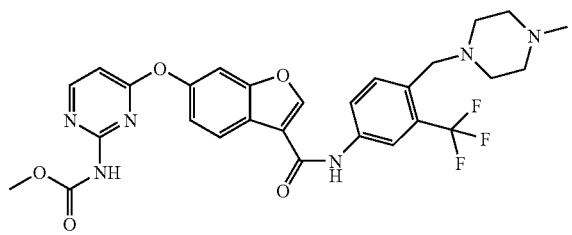

A solution of 124 mg (1.31 mMol) methyl chloroformiate in 1 ml $CH_2Cl_2$ is added to 289 mg (0.55 mMol) 6-(2-amino-pyrimidin-4-yloxy)-benzofuran-3-carboxylic acid [4-(4-methyl-piperazin-1-ylmethyl)-3-trifluoro-methyl-phenyl]-amide (Ex. 10j) dissolved in 2.3 ml $CH_2Cl_2$ and 2.3 ml pyridine. After 30 min, the mixture is concentrated in vacuo, the residue re-dissolved in EtOAc and a diluted $NaHCO_3$ solution, the aq. phase separated off and extracted twice with EtOAc. The organic layers are washed with water and brine, dried ($Na_2SO_4$), treated with char coal and concentrated. Trituration with EtOAc and ether gives the title compound: m.p.: 222-223° C.; Anal. (+0.3$H_2O$): C,H,N,F,O; IR: 1743 $cm^{-1}$ (carbamate), 1682 $cm^{-1}$ (amide), 1537 $cm^{-1}$ (amide).

Example 12

6-(2-Amino-pyrimidin-4-yloxy)-benzo[b]thiophene-3-carboxylic acid (3-trifluoromethyl-phenyl)-amide

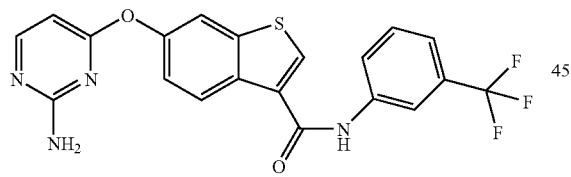

In a dried vessel, 66 mg (0.41 mMol) 3-trifluoromethyl-aniline are dissolved in 7 ml degassed toluene and cooled to 10° C. Then 650 μl $Me_3Al$ (2 M in toluene; 1.3 mMol) are added via syringe. After 45 min at rt, a solution of 100 mg (0.317 mMol) 6-(2-amino-pyrimidin-4-yloxy)-benzo[b]thiophene-3-carboxylic acid ethyl ester (Step 12.5) in 2.5 ml THF is added and the reaction mixture is stirred for 40 min in an oil bath of 110° C. The solution is cooled in an ice-bath and hydrolyzed with 15 ml of a sat. $NH_4Cl$. After 10 min stirring, the mixture is filtered through Celite, the solid washed extensively with EtOAc and water, the aq. phase separated from the filtrate and extracted with EtOAc. The organic layers are washed with water and brine, dried ($Na_2SO_4$) and concentrated. Column chromatography ($SiO_2$; EtOAc/hexane 9:1) and crystallization from $CH_2Cl_2$/hexane gives the title compound: MS: $[M+1]^+$=431; TLC(EtOAc/hexane 9:1): $R_f$=0.24.

The starting material is prepared as follows:

Step 12.1:
3-Methoxy-phenylsulfanyl)-2-oxo-propionic acid ethyl ester 28 g (0.20 Mol) 3-Methoxythiophenol are dissolved in 115 ml pyridine and cooled to 5° C. Then 25 ml (0.20 Mol) ethyl bromopyruvate are added dropwise during 40 min. The yellow suspension is stirred for 30 min at 5-8° C., then 250 ml of 4 N HCl are added (pH≈6). After dilution with 300 ml ether, the aq. layer is separated off, acidified with 4 N HCl to pH≈4 and extracted with 3 times 150 ml ether. The organic phases are washed with 3 portions of 1 N HCl, water and brine, dried ($Na_2SO_4$) and concentrated. This crude product is used as such in Step 12.2.

Step 12.2:
6-Methoxy-benzo[b]thiophene-3-carboxylic acid ethyl ester 306 g Polyphosphoric acid (Riedel-de-Haen 04101) are heated up to 70° C. Then 250 ml chlorobenzene are added, followed by a solution of 50.5 g (0.2 Mol) of crude 3-(3-methoxy-phenylsulfanyl)-2-oxo-propionic acid ethyl ester in 280 ml chlorobenzene. The mixture is heated up to 112° C. for 4 h. From the resulting 2-phasic hot mixture, the yellow-brownish upper layer is sucked off. The black lower phase is extracted by 3 portions of 250 ml boiling toluene. The upper layer and the 3 toluene extracts are combined and concentrated in vacuo (→crude 1). The residue from the black lower phase is hydrolysed in 7 l water. Extraction with 2 portions of $CH_2Cl_2$ gives more material (→crude 2). Both batches (crude 1 & 2) are combined and diluted with $CH_2Cl_2$, water and sat. $NaHCO_3$. The aq. phase is separed off and extracted twice with $CH_2Cl_2$. The organic layers are washed twice with water and brine, dried ($Na_2SO_4$) and concentrated. Column chromatography ($SiO_2$; hexane/$CH_2Cl_2$ 9:1→7:3→1:1) and crystallization from hexane at −20° C. gives the title compound: m.p.: 68-69° C.; TLC(hexane/acetone 4:1): $R_f$=0.47.

Step 12.3:
6-Hydroxy-benzo[b]thiophene-3-carboxylic acid ethyl ester

To a solution of 4.72 g (20 mMol) 6-methoxy-benzo[b]thiophene-3-carboxylic acid ethyl ester in 200 ml $CH_2Cl_2$ at −10° C., 40 ml of a 1 M solution of $BBr_3$ in $CH_2Cl_2$ are added via syringe during 12 min. The solution is stirred for 3.5 h at −10 to 0° C., then diluted with 600 ml EtOAc and poured into 450 ml of a mixture of sat. $NaHCO_3$ and ice. After 5 min, the aq. layer is separated off and extracted 3× with 120 ml EtOAc. The organic phases are washed with water and brine, dried ($Na_2SO_4$) and after addition of $SiO_2$ concentrated. The resulting powder is put on top of a $SiO_2$-column and the title compound eluted with hexan/EtOAc 4:1: m.p.: 128-129° C.; TLC(hexane/EtOAc 4:1): $R_f$=0.18.

Step 12.4: 6-(2-Amino-6-chloro-pyrimidin-4-yloxy)-benzo[b]thiophene-3-carboxylic acid ethyl ester A mixture of 2.563 g (11.5 mMol) 6-hydroxy-benzo[b]thiophene-3-carboxylic acid ethyl ester, 3.06 g (18.5 mMol) 2-amino-4,6-dichloropyrimidine and 5.15 g (23 mMol) $K_3PO_4$ in 87 ml NMP is stirred for 1.5 h at 60° C. Then the mixture is poured into EtOAc and water, the aq. layer separated off and extracted 3 times with EtOAc. The organic phases are washed with water and brine, dried ($Na_2SO_4$) and concentrated. Trituration in ether and filtration gives the title compound: m.p.: 178-179° C.; TLC(hexane/EtOAc 2:1): $R_f$=0.27. More product can be obtained from the filtrate by column chromatography ($SiO_2$; hexane/EtOAc 3:1).

Step 12.5: 6-(2-Amino-pyrimidin-4-yloxy)-benzo[b]thiophene-3-carboxylic acid ethyl ester A solution of 3.70 g (10.6 mMol) 6-(2-amino-6-chloro-pyrimidin-4-yloxy)-benzo[b]thiophene-3-carboxylic acid ethyl ester in 300 ml THF and 8.68 ml (108 mMol) pyridine is hydrogenated in presence of 3.0 g Pd/C (10%; added in 3 portions during 23 h). The mixture is filtered and the solid washed extensively with MeOH. The filter cake still contains product and is therefore stirred in EtOAc and water. The separated EtOAc layer is washed twice with water, added to the filtrate and concentrated. The residue is re-dissolved in 300 ml EtOAc and 50 ml MeOH. Then water is added, the aq. layer separated off and extracted 4× with EtOAc. The organic layers are washed with water and brine, dried ($Na_2SO_4$) and concentrated together with 21 g $SiO_2$. The resulting powder is put on top of a $SiO_2$-column and the title compound eluated with EtOAc/hexane 9:1: m.p.: 144-145° C.; TLC(EtOAc/hexane 9:1): $R_f$=0.27.

Example 13

The following derivatives are obtained analogously to Ex. 12.

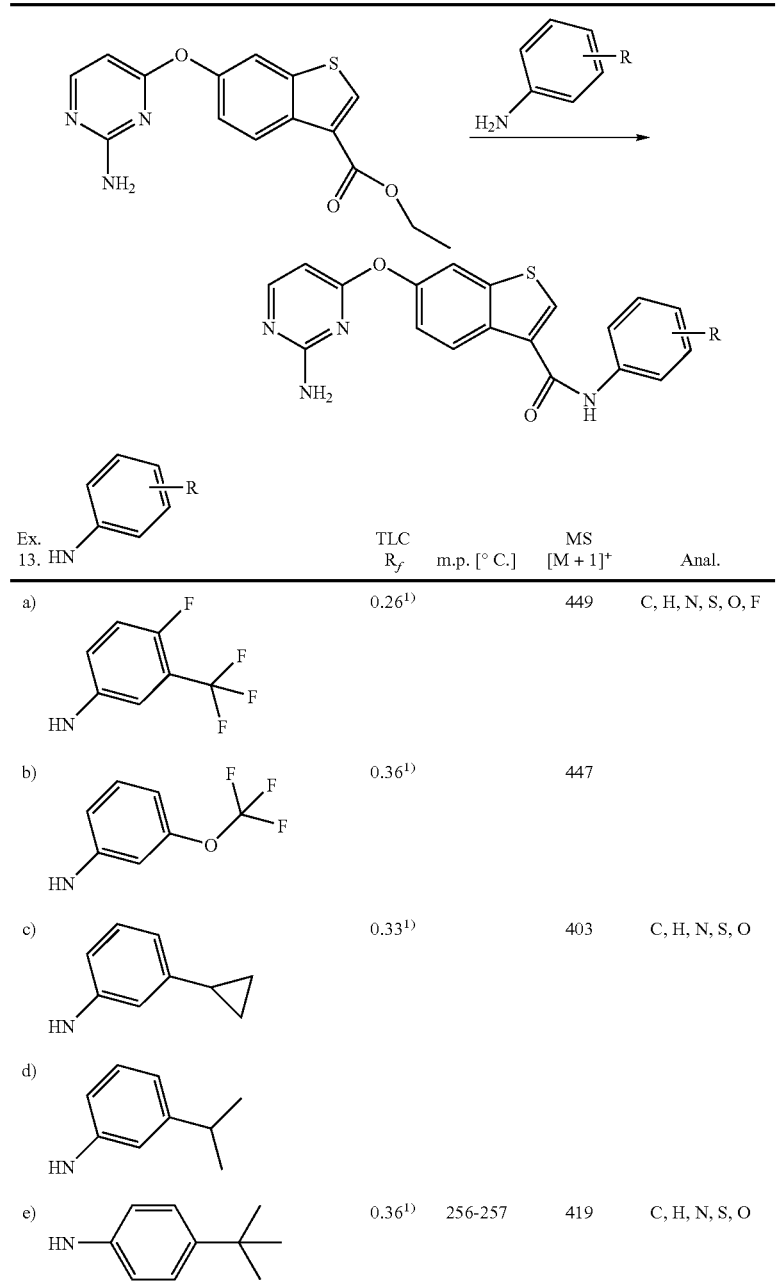

-continued
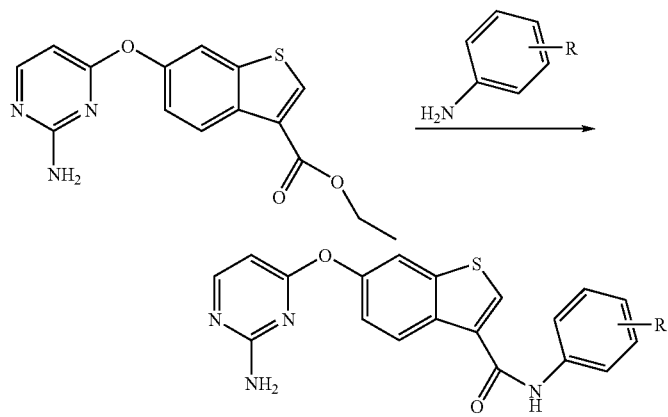
| Ex. 13. | HN-Ar(R) | TLC $R_f$ | m.p. [° C.] | MS $[M+1]^+$ | Anal. |
|---|---|---|---|---|---|
| f) | 3,4-dimethylphenyl | 0.31[1] | 210-211 | 391 | C, H, N, S, O |
| g) | 3,5-dimethoxyphenyl | | | | |
| h) | 4-methyl-3-trifluoromethylphenyl | | | | |
| i) | 3-tert-butylphenyl | 0.37[1] | | 419 | |
| j) | 3-phenoxyphenyl | | | | |
| k) | 4-(4-methylpiperazin-1-ylmethyl)-3-trifluoromethylphenyl | 0.37[2] | 195-198 | 543 | C, H, N, S, O, F |
[1] EtOAc/hexane 9:1;
[2] EtOAc;
[3] CH$_2$Cl$_2$/MeOH/$^{conc.}$NH$_3^{aq.}$ 90:10:1

Example 14

(4-{3-[4-(4-Methyl-piperazin-1-ylmethyl)-3-trifluoromethyl-phenylcarbamoyl]-benzo[b]thiophene-6-yloxy}-pyrimidin-2-yl)-carbamic acid methyl ester

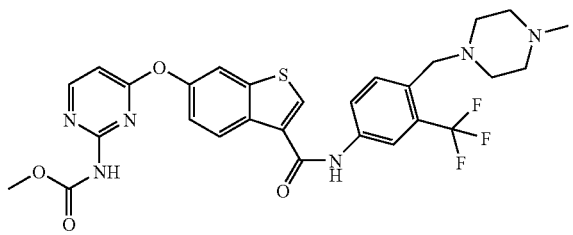

Prepared analogously as described in Ex. 11 from 6-(2-amino-pyrimidin-4-yloxy)-benzo[b]thiophene-3-carboxylic acid [4-(4-methyl-piperazin-1-ylmethyl)-3-trifluoro-methyl-phenyl]-amide (Ex. 13k) and methyl-chloroformate in $CH_2Cl_2$ and pyridine: m.p.: 205-206° C.; Anal. (+0.3$H_2O$): C,H,N,S,F,O.

Example 15

6-(2-Amino-pyrimidin-4-yloxy)-pyrazolo[1,5-a]pyridine-3-carboxylic acid (3-trifluoromethyl-phenyl)-amide

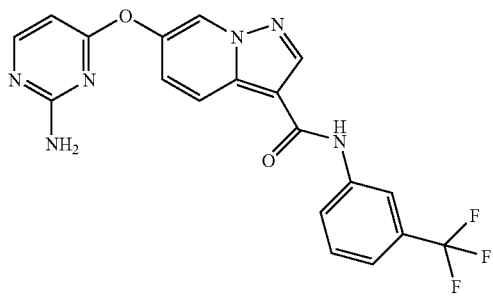

27 mg (0.064 mMol) 6-(2-Amino-6-chloro-pyrimidin-4-yloxy)-pyrazolo[1,5-a]pyridine-3-carboxylic acid (3-trifluoromethyl-phenyl)-amide are dissolved in 2 ml THF and submitted to hydrogenation over Pd—C (Engelhardt 4045) for 2 h at rt. The reaction mixture is worked up by filtration and concentrated to give the title compound as a white solid: m.p.: 102-104° C.; MS: $[M+1]^+$=415.

The starting material is prepared as follows:

Step 15.1: 3-Benzyloxy-pyridine 9.5 g (10 mMol) 3-Hydroxy-pyridine and 9.45 ml (10 mMol) benzylchloride are dissolved in 50 ml $CH_2Cl_2$ at rt. 0.5 g Adogen 464® (Aldrich 63393-96-4) are added followed by dropwise addition of 50 ml of aq. NaOH solution (40% wt). The resulting yellow solution is stirred overnight, leading to formation of a white precipitate. The insolubles are filtered off and the filtrated is diluted with $CH_2Cl_2$ and $H_2O$. The phases are separated and the aq. phase is repeatedly extracted with $CH_2Cl_2$. Combined organic extracts are dried, concentrated and the residual crude product is purified by flash chromatography ($SiO_2$, $CH_2Cl_2$/MeOH 95:5) to give the title compound as a yellow oil: MS: $[M+1]^+$=186; $^1$H MNR ($CDCl_3$): δ ppm 8.42 (s, 1H), 8.26 (s, 1H), 7.55-7.38 (m, 5H), 7.30-7.19 (m, 2H), 5.17 (s, 2H).

Step 15.2: Ethyl-O-mesitylenesulfonylacetohydroxamate

Prepared according to lit. procedure (*Tet Lett.* 1972, 40, 4133-4135). 15 g (68.6 mMol) Mesitylen-2-sulfonylchloride and 10.5 ml (75.5 mMol) triethyl amine are dissolved in 80 ml DMF. The solution is cooled to 0° C. in an ice bath and 7.1 g (68.6 mMol) ethyl-N-hydroxyacetimidate are added in small portions. The reaction mixture is subsequently stirred for 3 h at rt, filtered and concentrated. The residue is first washed with ether and then submitted to aq. workup with EtOAc/$H_2O$. Combined organic extracts are dried and concentrated to give the title compound as yellow oil: MS: $[M+1]^+$=286; $^1$H MNR ($CDCl_3$): δ ppm 7.00 (s, 2H), 3.98 (q, 2H), 2.64 (s, 6H), 2.39 (s, 3H), 2.05 (s, 3H), 1.21 (t, 3H).

Step 15.3: O-Mesitylenesulfonylacetohydroxylamine

Prepared according to lit. procedure (*Tet Lett.* 1972, 40, 4133-4135). 7.85 g (28.1 mMol) Ethyl-O-mesitylenesulfonylacetohydroxamate are added to 50 ml perchloric acid (60%, Fluka 77232) and stirred for 1 h at rt. The reaction is then concentrated under reduced pressure to give the title compound as a white powder: MS: $[M+1]^+$=217; $^1$H MNR ($CDCl_3$): δ ppm 7.02 (s, 2H), 6.61 (bs, 2H, NH2), 2.62 (s, 6H), 2.39 (s, 3H).

Step 15.4: 2,4,6-Trimethyl-benzenesulfonate-1-amino-3-benzyloxy-Pyridinium 8.75 g (40.6 mMol) O-Mesitylenesulfonylacetohydroxylamine and 4.2 g (22.7 mMol) 3-benzyloxy-pyridine are dissolved in 70 ml $CH_2Cl_2$ and stirred for 2 h at rt. The reaction mixture is diluted with ether leading to precipitation of the product which is isolated by filtration, washed with ether and dried to give the title compound as a white powder: $^1$H MNR ($CDCl_3$): δ ppm 9.01 (s, 1H), 8.76 (d, 1H), 7.58 (dd, 1H), 7.41 (d, 1H), 7.40-7.38 (m, 5H), 6.84 (s, 2H), 5.18 (s, 2H), 2.74 (s, 6H), 2.22 (s, 3H).

Step 15.5: 6-Benzyloxypyrazolo[1r5-a]pyridine-3-carboxylic acid methyl ester 3.2 g (8 mMol) 2,4,6-Trimethyl-benzenesulfonate-1-amino-3-benzyloxy-pyridinium are dissolved in 15 ml $CHCl_3$ and cooled to 0° C. 1.6 g (12 mMol) $K_2CO_3$ (puriss>99%, Fluka 60109) and 1.3 ml (16 mMol) methyl propiolate are added and the mixture is stirred at rt for 18 h. It is worked up by filtration and the filtrate is concentrated under reduced pressure. The remaining crude product is purified by flash chromatography ($SiO_2$; 120 g column, hexanes/EtOAc, gradient 0-30% EtOAc) to give the title compound as a yellow solid: MS: $[M+1]^+$=283; $^1$H MNR ($CDCl_3$): δ ppm 8.39 (s, 1H), 8.21 (s, 1H), 8.02 (d, 1H), 7.59-7.39 (m, 5H), 7.25 (d, 1H), 5.16 (s, 2H), 3.97 (s, 3H).

Step 15.6: 6-Hydroxypyrazolo[1,5-a]pyridine-3-carboxylic acid methyl ester 101 mg Product from Step 15.5 (0.36 mMol) are dissolved in 5 ml HOAc and treated with 0.31 ml HBr (5.7 M solution in HOAc) at rt. The reaction mixture is stirred for 1 h at 119° C. It is then cooled to rt again, diluted with EtOAc and $H_2O$ and the organic layer is separated. The aq. phase is repeatedly extracted with EtOAc and combined organic extracts are dried and concentrated to give the title compound as an off-white solid: MS: $[M+1]^+$=193; $^1$H MNR ($CD_3OD$): δ ppm 8.24 (s, 1H), 8.19 (s, 1H), 7.99 (d, 1H), 7.24 (d, 1H), 3.84 (s, 3H).

Step 15.7: 6-(2-Amino-6-chloro-pyrimidin-4-yloxy)-pyrazolo[1,5-a]pyridine-3-carboxylic acid methyl ester 58.9 mg Product from Step 15.6 (0.31 mMol) are dissolved in 8 ml NMP and treated with 268 mg (1.2 mMol) K₃PO₄ and 75 mg (0.46 mMol) 2-amino-4,6-dichloropyrimidine at rt. The reaction mixture is warmed to 70° C. and stirred for 20 h at rt. It is worked up by addition of EtOAc and washed with H₂O. The organic layer is dried and concentrated to give the crude product which is purified by recrystallization from EtOAc to give the title compound as a white powder: MS: [M+1]$^+$=320; $^1$H MNR (DMSO-d6): δ ppm 9.18 (s, 1H), 8.43 (s, 1H), 8.09 (d, 1H), 7.60 (d, 1H), 7.21 (bs, 2H, NH₂), 6.42 (s, 1H), 3.82 (s, 3H).

Step 15.8: 6-(2-Amino-6-chloro-pyrimidin-4-yloxy)-pyrazolo[1,5-a]pyridine-3-carboxylic acid (3-trifluoromethyl-phenyl)-amide 10.5 μl (0.084 mMol) 3-Trifluoromethyl aniline are dissolved in 2 ml toluene and cooled to 5° C. 126 μl Me₃Al (2 M solution in toluene; 0.25 mMol) are added slowly via a syringe followed by a solution of 27 mg (0.084 mMol) 6-(2-amino-6-chloro-pyrimidin-4-yloxy)-pyrazolo[1,5-a]pyridine-3-carboxylic acid methyl ester in 1 ml THF. The reaction is stirred at rt for 1 h and then heated to 110° C. for 30 min. The reaction is submitted to aq. workup with EtOAc/H₂O. The organic layers are combined, dried and concentrated to give the crude product which is further purified by flash chromatography (SiO₂, 4 g column, CH₂Cl₂/MeOH; gradient 0-10% MeOH) to give the title compound as a white solid: m.p.: 219-221° C.; MS: [M+1]$^+$=449.

Example 16

The following derivatives are obtained analogously to Ex. 15.

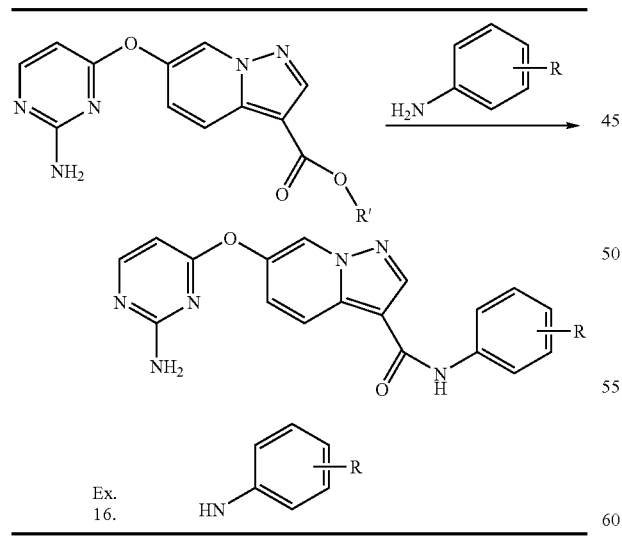

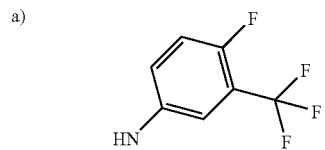

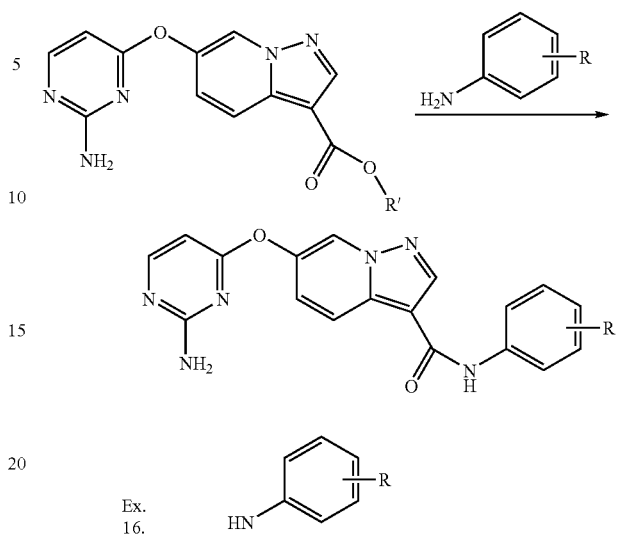

b) 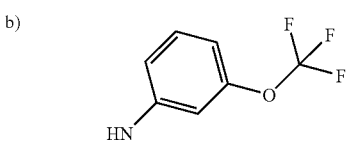

c) 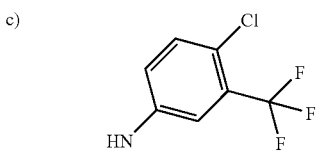

d) 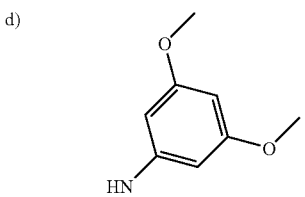

e) 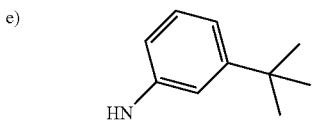

f) 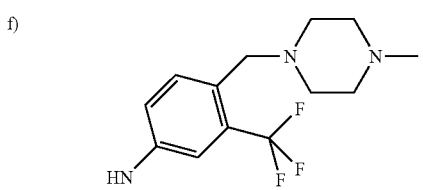

g) 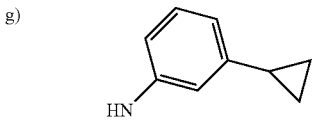

Example 17

6-(2-Hydroxymethyl-pyrimidin-4-yloxy)-benzo[b]thiophene-3-carboxylic acid (3-tert-butyl-phenyl)-amide

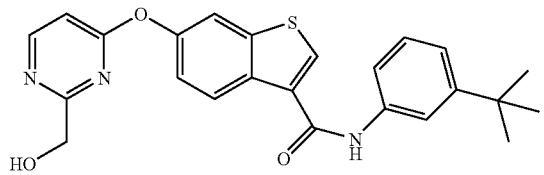

In a dried vessel, 82 mg (0.55 mMol) 3-tert-butyl-aniline are dissolved in 8 ml toluene and cooled in an ice bath. Then 825 μl Me$_3$Al (2 M in toluene; 1.65 mMol) are added via syringe. After 1¼ h at rt, a solution of 107 mg (0.25 mMol) 6-(2-hexanoyloxymethyl-pyrimidin-4-yloxy)-benzo[b]thiophene-3-carboxylic acid ethyl ester (Step 17.5) in 1 ml THF is added and the solution is stirred for 1 h in an oil bath of 110° C. The solution is cooled in an icebath and hydrolyzed with 16 ml of a sat. NH$_4$Cl solution. After 15 min stirring, the mixture is diluted with EtOAc and water, the aq. phase separated off and extracted twice with EtOAc. The organic layers are washed with water and brine, dried (Na$_2$SO$_4$) and concentrated. Chromatography (Combi Flash; hexane/EtOAc 9:1→1:1→EtOAc) gives the title compound: Anal. (+0.3H$_2$O): C,H,N,S; MS: [M+1]$^+$=434; TLC(hexane/EtOAc 1:2): R$_f$=0.31; $^1$H MNR (DMSO-d6): δ ppm 10.32 (s, HN), 8.67 (d, 1H), 8.58 (s, 1H), 8.46 (d, 1H), 8.03 (s, 1H), 7.76 (s, 1H), 7.68 (d, 1H), 7.35 (d, 1H), 7.28 (t, 1H), 7.15 (d, 1H), 6.98 (d, 1H), 5.18 (sb, HO), 4.41 (s, CH$_2$), 1.31 (s, 9H).

The starting material is prepared as follows:

Step 17.1: 4-Methoxy-pyrimidine-2-carboxylic acid ethyl ester

A mixture of 10 g (69.2 mMol) 2-chloro-4-methyoxy-pyrimidine, 19.6 ml (0.14 Mol) Et$_3$N and 2.42 g (3.45 mMol) PdCl$_2$(Ph$_3$P)$_2$ in 100 ml EtOH is heated in an autoclave at 100° C. for 15 h under an atmosphere of ≈100 bar of CO-gas. After cooling to rt, the mixture is filtered and the filtrate concentrated. The residue is dissolved in EtOAc and water, the aq. phase is separated off and extracted twice with EtOAc. The organic layers are washed with water and brine, dried (Na$_2$SO$_4$) and concentrated. Chromatography [Combi Flash; (hexane/CH$_2$Cl$_2$ 1:1)/EtOAc 9:1→1:1] gives the title compound: MS: [M+1]$^+$=183; TLC(hexane/EtOAc 1:1): R$_f$=0.28.

Step 17.2: Hexanoic acid 4-methoxy-pyrimidin-2-ylmethyl ester

To a solution of 3.7 g (20.3 mMol) 4-methoxy-pyrimidine-2-carboxylic acid ethyl ester in 37 ml of tert-butanol, 2.3 g (61 mMol) of NaBH$_4$ are added. The mixture is stirred at 60° C. for 5 h and cooled to rt. 15 min after quenching with 5 ml of acetone, the mixture is poured into 20 ml of a sat. NaHCO$_3$ solution and 0.4 l EtOAc and stirred for 20 min. The inorganic phase is separated off and extracted twice with EtOAc. The organic layers are washed with 20 ml of a 1:1 mixture of brine and water, dried (Na$_2$SO$_4$) and concentrated, yielding (4-methoxy-pyrimidin-2-yl)-methanol (MS: [M+1]$^+$=141).

The crude (4-methoxy-pyrimidin-2-yl)-methanol is dissolved in 30 ml CH$_2$Cl$_2$ and 10 ml pyridine. Then 8.7 g (40.6 mMol) caproic anhydride and 20 mg DMAP are added and the solution is stirred for 4 h at rt. After addition of 5 ml of isopropanol stirring is continued for 15 min. The reaction mixture is diluted with water and EtOAc, the aq. phase separated off and extracted twice with EtOAc. The organic layers are washed twice with water and brine, dried (Na$_2$SO$_4$) and concentrated. Column chromatography (SiO$_2$; hexane/EtOAc 3:1→2:1) gives the title compound: MS: [M+1]$^+$=239; TLC(hexane/EtOAc 2:1): R$_f$=0.38.

Step 17.3: Hexanoic acid 4-hydroxy-pyrimidin-2-ylmethyl ester 3.1 g (13.0 mMol) hexanoic acid 4-methoxy-pyrimidin-2-ylmethyl ester and 5.85 g (39 mMol) NaI are dissolved in 130 ml (13 mMol) of a 0.1 M solution of water in acetonitrile at 60° C. Then 4.95 ml (39 mMol) Me$_3$SiCl are added via syringe. The resulting suspension is stirred for 7 h at 60° C. and then cooled to rt again. Then 15 ml of MeOH are added dropwise. After stirring for 10 additional minutes, the reddish suspension is concentrated in vacuo. The residue is redissolved in 300 ml EtOAc and 100 ml sat. NaHCO$_3$ solution, the aq. layer separated off and extracted with 2×300 ml EtOAc. The organic phases are washed with 50 ml of a 0.5 M solution of Na$_2$S$_2$O$_3$ and brine, dried (Na$_2$SO$_4$) and concentrated. Crystallization from CH$_2$Cl$_2$ and hexane gives the title compound: m.p.: 78° C.; MS: [M+1]$^+$=225.

Step 17.4: Hexanoic acid 4-chloro-pyrimidin-2-ylmethyl ester

To a solution of 300 mg (1.33 mMol) hexanoic acid 4-hydroxy-pyrimidin-2-ylmethyl ester, 487 mg (2.94 mMol) Et$_4$NCl and 373 μl (2.94 mMol) N,N-dimethylaniline in 15 ml of acetonitrile, 1.22 ml (13.3 mMol) POCl$_3$ are added. After stirring for 24 h at rt, the solution is concentrated in vacuo. The residue is re-dissolved in EtOAc and sat. NaHCO$_3$, the aq. layer separated off and extracted twice with EtOAc. The organic phases are dried (Na$_2$SO$_4$) and concentrated. Chromatography (Combi Flash; hexane/ether 199:1→9:1→3:2) gives the title compound as an oil: MS: [M+1]$^+$=243/245; TLC(CH$_2$Cl$_2$): R$_f$=0.26.

Step 17.5: 6-(2-Hexanoyloxymethyl-pyrimidin-4-yloxy)-benzo[b]thiophene-3-carboxylic acid ethyl ester A suspension of 324 mg (1.33 mMol) hexanoic acid 4-chloro-pyrimidin-2-ylmethyl ester, 313 mg (1.41 mMol) 6-hydroxy-benzo[b]thiophene-3-carboxylic acid ethyl ester (Step 12.3) and 312 mg (1.47 mMol) K$_3$PO$_4$ in 5 ml NMP is stirred for 45 h at 60° C. The reaction mixture is dissolved in water and EtOAc, the aq. phase separated off and extracted twice with EtOAc. The organic layers are washed with water and brine, dried (Na$_2$SO$_4$) and concentrated. Chromatography (Combi Flash; CH$_2$Cl$_2$/ether 59:1→9:1) and crystallization from hexane gives the title compound: m.p.: 51° C.; MS: [M+1]$^+$=429; TLC(CH$_2$Cl$_2$/ether 19:1): R$_f$=0.28.

Example 18
The following derivatives are obtained analogously to Ex. 17.
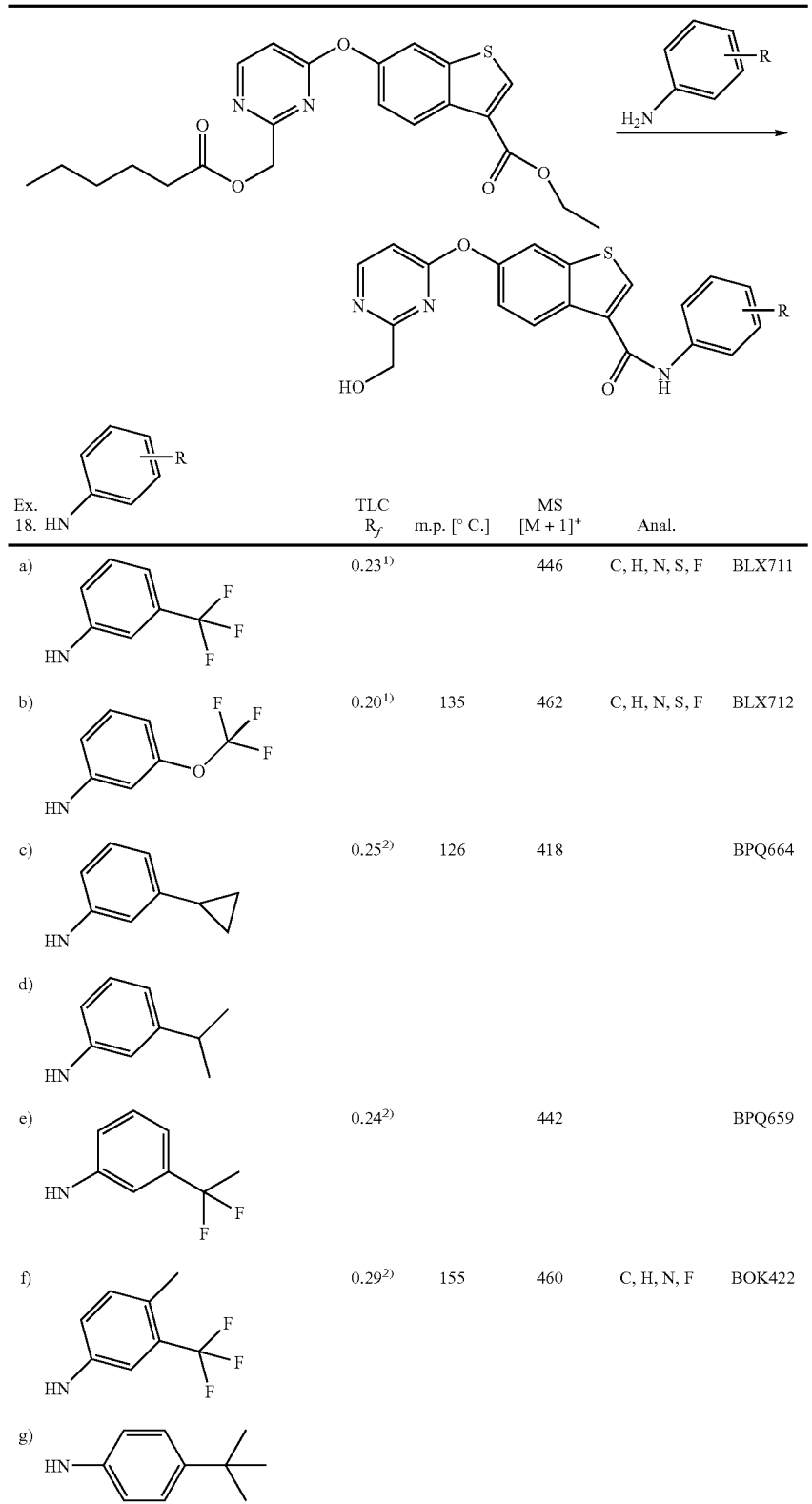
| Ex. 18. HN-R | TLC $R_f$ | m.p. [°C.] | MS [M + 1]+ | Anal. | |
|---|---|---|---|---|---|
| a) 3-CF3-phenyl | 0.23[1] | | 446 | C, H, N, S, F | BLX711 |
| b) 3-OCF3-phenyl | 0.20[1] | 135 | 462 | C, H, N, S, F | BLX712 |
| c) 3-cyclopropyl-phenyl | 0.25[2] | 126 | 418 | | BPQ664 |
| d) 3-isopropyl-phenyl | | | | | |
| e) 3-CHF2-CH3-phenyl | 0.24[2] | | 442 | | BPQ659 |
| f) 4-methyl-3-CF3-phenyl | 0.29[2] | 155 | 460 | C, H, N, F | BOK422 |
| g) 4-tBu-phenyl | | | | | |

-continued

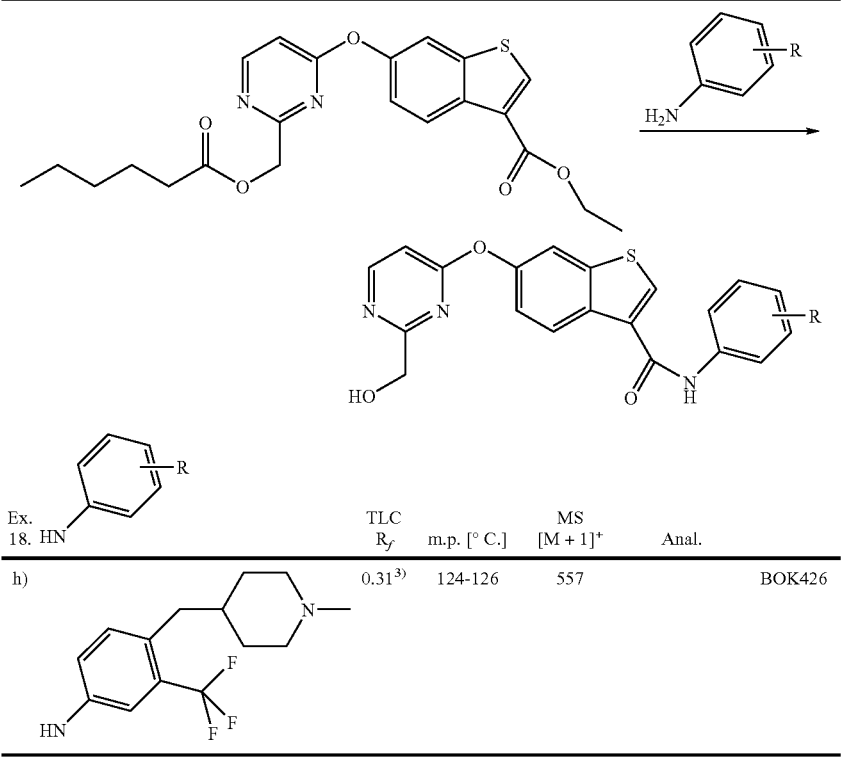

| Ex. | | TLC $R_f$ | m.p. [° C.] | MS [M + 1]+ | Anal. |
|---|---|---|---|---|---|
| 18. h) |  | 0.31[3)] | 124-126 | 557 | BOK426 |

[1)]EtOAc/hexane 2:1;
[2)]EtOAc/hexane 7:3;
[3)]$CH_2Cl_2/MeOH/^{conc.}NH_3^{aq.}$ 80:20:1

Example 19

6-(6-Hydroxymethyl-pyrimidin-4-yloxy)-benzo[b]thiophene-3-carboxylic acid (4-fluoro-3-trifluoromethyl-phenyl)-amide In a dried vessel, 120 μl (0.93 mMol) (4-fluoro-3-trifluoromethyl)-aniline are dissolved in 15.5 ml toluene and cooled in an ice bath. Then 930 μl $Me_3Al$ (2 M in toluene; 1.86 mMol) are added via syringe. After 1 h at rt, a solution of 200 mg (0.467 mMol) 6-(4-hexanoyloxymethyl-pyrimidin-6-yloxy)-benzo[b]thiophene-3-carboxylic acid ethyl ester (Step 19.6) in 4.6 ml THF is added and the solution is stirred for 1 h in an oil bath of 110° C. The solution is cooled in an icebath and hydrolyzed with 20 ml of a sat. $NH_4Cl$ solution and 10 ml water. After 10 min stirring, the mixture is diluted with EtOAc and water, the aq. phase separated off and extracted twice with EtOAc. The organic layers are washed with water and brine, dried ($Na_2SO_4$) and concentrated. Chromatography ($SiO_2$; hexane/EtOAc 3:1) and crystallization from hexane gives the title compound: m.p.: 138-140° C.; MS: [M+1]+=464; $^1$H MNR (DMSO-d6): δ ppm 10.72 (s, HN), 8.66 (s, 1H), 8.64 (s, 1H), 8.48 (d, 1H), 8.27 (m, 1H), 8.09 (m, 1H), 8.05 (s, 1H), 7.56 (t, 1H), 7.36 (d, 1H), 7.07 (s, 1H), 5.68 (t, HO), 4.55 (d, $CH_2$).

The starting material is prepared as follows:

Step 19.1: Isopropyl Formimidate Hydrochloride

A solution of 34.8 ml (300 mMol) benzoylchloride in 250 ml ether is cooled to 10-20° C. Then a solution of 23 ml (301 mMol) isopropanol and 11.9 ml (301 mMol) formamide is added dropwise during 45 min. The resulting suspension is stirred for another 2 h and then filtered. Washing of the residue with ether gives the title compound: $^1$H MNR (DMSO-d6): δ ppm 11.55 (sb, 2H), 8.72 (s, 1H), 5.03 (sept, 1H), 1.33 (d, 6H).

Step 19.2: N-tert-Butyldimethylsilyl Isopropyl Formimidate 8.2 g (66.4 mMol) isopropyl formimidate hydrochloride suspended in 80 ml $CH_2Cl_2$ are cooled to −40° C. Then 20.3 ml (146 mMol) $Et_3N$ are added dropwise during 5 min at −40° C., followed by a solution of 15.2 ml (66.1 mMol) tert-butyldimethylsilyl trifluoromethansulfonate in 40 ml $CH_2Cl_2$ during 10 min. After 15 min stirring at −40° C., 100 ml of hexane are added to the white suspension. Warming up to rt, filtration, washing with hexane and concentration of the filtrate gives the crude product. Re-dissolving in ether, filtration and concentration gives the title compound: $^1$H MNR (DMSO-$d_6$): δ ppm 7.67 (s, 1H), 4.98 (sept, 1H), 1.15 (d, 6H), 0.82 (s, 9H), 0.02 (s, 6H).

Step 19.3: 6-Hydroxy-pyrimidine-4-carboxylic acid ethyl ester [L. Ghosez et al., Tetrahedron 55 (1999), 3387]

2.80 g (13.9 mMol) N-tert-butyldimethylsilyl isopropyl formimidate are dissolved in 8 ml toluene and cooled to 10°

C. Then 2.32 ml (16.7 mMol) Et₃N are added via syringe, followed by a solution of 989 μl (13.9 mMol) acetylchloride in 3 ml toluene. After stirring the resulting suspension for 2 h at rt, 30 ml of hexane are added. Filtration and concentration of the filtrate gives methanimidic acid, N-[1-[[(1,1-dimethylethyl)dimethylsilyl]oxy]ethenyl]-,1-methylethyl ester (MS: [M+1]$^+$=244).

This intermediate is re-dissolved in 15 ml toluene and 3.27 ml (33.4 mMol) nitriloacetic acid ethyl ester are added. The mixture is heated for 3 h at 83° C. After addition of 30 ml MeOH, the solution is stirred for 3 h at 75° C. and then cooled to rt and concentrated in vacuo. Crystallization from 50 ml ether gives the title compound: m.p.: 193-194° C.; MS: [M+1]$^+$=169; Anal.: C,H,N,O.

Step 19.4: Hexanoic acid 6-hydroxy-pyrimidin-4-ylmethyl ester

To a suspension of 1.7 g (10.1 mMol) 6-hydroxy-pyrimidine-4-carboxylic acid ethyl ester in 30 ml of tert-butanol, 1.2 g (31 mMol) of NaBH₄ are added. The mixture is stirred at 60° C. for 20 h and cooled to rt. Then 45 ml of acetone are added. After stirring for 15 min, the mixture is concentrated in vacuo. The residue is diluted with toluene and again concentrated, yielding (6-hydroxy-pyrimidin-4-yl)-methanol (MS: [M−1]=125).

The crude (6-hydroxy-pyrimidin-4-yl)-methanol is diluted with 60 ml CH₂Cl₂ and 20 ml pyridine. Then 9.3 ml (40 mMol) caproic anhydride and 49 mg DMAP are added and the suspension is stirred for 1 h at rt. The reaction mixture is diluted with water and EtOAc, the aq. phase separated off and extracted twice with EtOAc. The organic layers are washed 3 times with water and brine, dried (Na₂SO₄) and concentrated. Column chromatography (SiO₂; CH₂Cl₂/EtOH 19:1) gives after crystallization from CH₂Cl₂/hexane the title compound: m.p.: 133-134° C.; MS: [M+1]$^+$=225.

Step 19.5: Hexanoic acid 6-chloro-pyrimidin-4-ylmethyl ester

To a solution of 915 mg (4.08 mMol) hexanoic acid 6-hydroxy-pyrimidin-4-ylmethyl ester, 1.48 g (8.98 mMol) Et₄NCl and 698 μl (5.44 mMol) N,N-dimethylaniline in 30 ml of acetonitrile, 3.73 ml (40.8 mMol) POCl₃ are added. After stirring for 1 h at 60° C., the cooled solution is concentrated in vacuo. The residue is re-dissolved in EtOAc and water, the aq. layer separated off and extracted twice with EtOAc. The organic phases are washed with water, sat. NaHCO₃ and brine, dried (Na₂SO₄) and concentrated, yielding the title compound as an oil: MS: [M+1]$^+$=243/245; TLC (CH₂Cl₂): R$_f$=0.20.

Step 19.6: 6-(4-Hexanoyloxymethyl-pyrimidin-6-yloxy)-benzo[b]thiophene-3-carboxylic acid ethyl ester A suspension of 984 mg (4.05 mMol) hexanoic acid 6-chloro-pyrimidin-4-ylmethyl ester, 751 mg (3.38 mMol) 6-hydroxy-benzo[b]thiophene-3-carboxylic acid ethyl ester (Step 12.3) and 1.43 g (6.76 mMol) K₃PO₄ in 20 ml NMP is stirred for 1.5 h at 60° C. The reaction mixture is dissolved in water and EtOAc, the aq. phase separated off and extracted twice with EtOAc. The organic layers are washed with water and brine, dried (Na₂SO₄) and concentrated. Chromatography (SiO₂; hexane/EtOAc 4:1→1:1) gives the title compound: MS: [M+1]$^+$=429; TLC(hexane/EtOAc 4:1): R$_f$=0.14.

Example 20

The following derivatives are obtained analogously to Ex. 19.

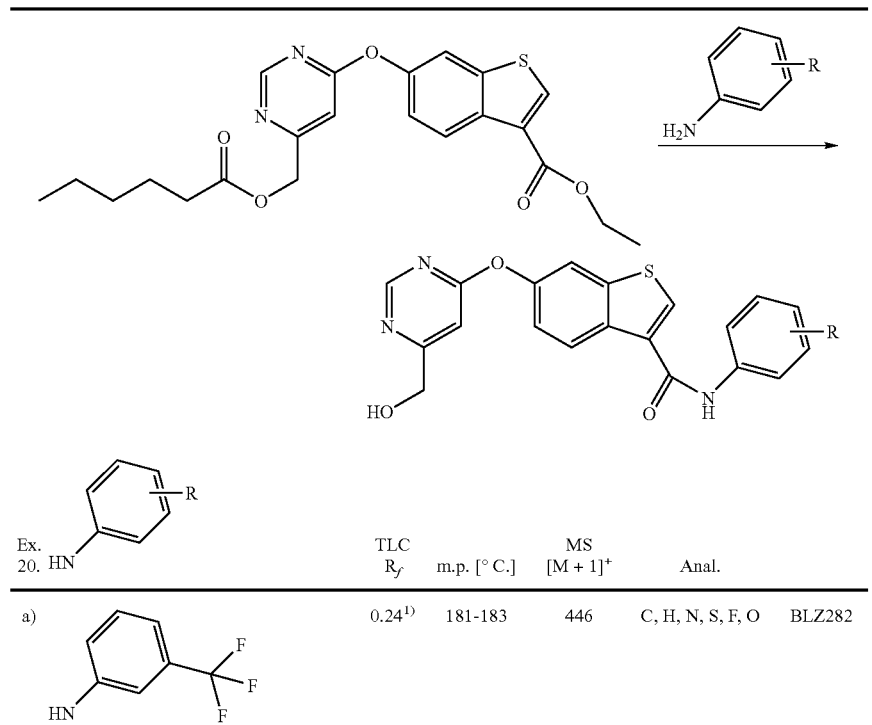

| Ex. 20. | TLC R$_f$ | m.p. [° C.] | MS [M + 1]$^+$ | Anal. | |
|---|---|---|---|---|---|
| a) | 0.24[1)] | 181-183 | 446 | C, H, N, S, F, O | BLZ282 |

-continued
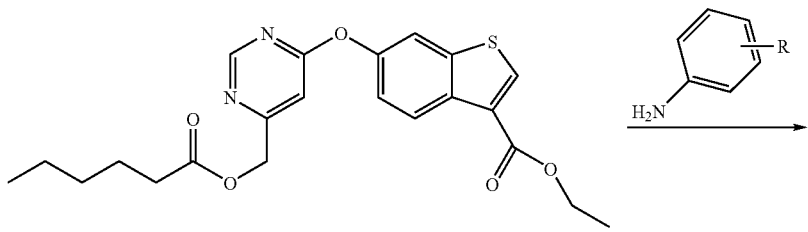
| Ex. 20. | HN-Ar-R | TLC $R_f$ | m.p. [° C.] | MS $[M + 1]^+$ | Anal. | |
|---|---|---|---|---|---|---|
| b) | 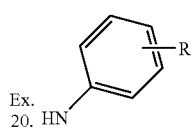 | 0.25[2)] | 190-193 | 462 | C, H, N, S, F, O | BLZ080 |
| c) | | | | | | |
| d) | 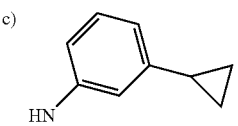 | 0.30[1)] | 108-110 | 434 | C, H, N, S, O | BLZ589 |
| e) | | | | | | |
| f) | 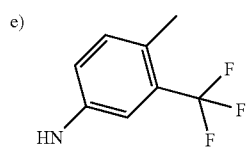 | 0.27[2)] | | 434 | C, H, N, S, O | BLY963 |

-continued

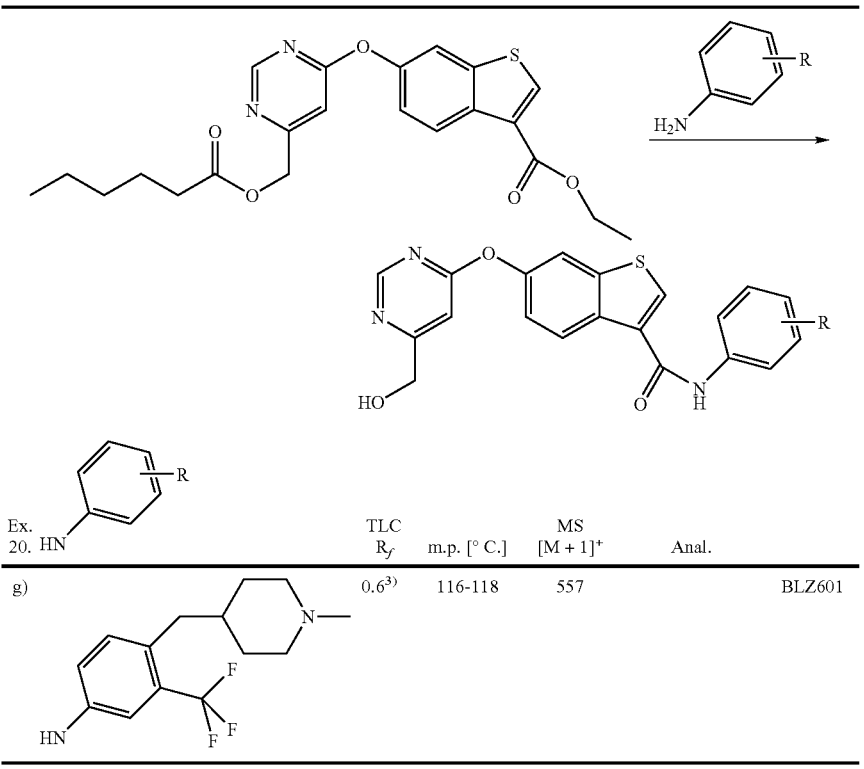

| Ex. | HN-R | TLC $R_f$ | m.p. [° C.] | MS $[M + 1]^+$ | Anal. | |
|---|---|---|---|---|---|---|
| 20. g) | 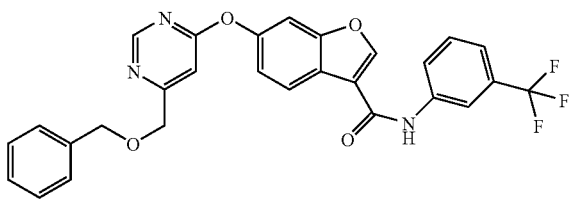 | 0.6[3)] | 116-118 | 557 | | BLZ601 |

[1)]toluene/acetone 4:1;
[2)]EtOAc/hexane 3:1;
[3)]$CH_2Cl_2$/MeOH/$^{conc.}NH_3^{aq.}$ 80:20:1

Example 21

6-(6-Benzyloxymethyl-pyrimidin-4-yloxy)-benzofuran-3-carboxylic acid (3-trifluoromethyl-phenyl)-amide In a dried vessel, 55 μl (0.44 mMol) 3-trifluoromethyl-aniline are dissolved in 6 ml toluene and cooled in an ice bath. Then 0.66 ml $Me_3Al$ (2 M in toluene; 1.32 mMol) are added via syringe. After 1 h at rt, a solution of 156 mg (0.40 mMol) 6-(6-benzyloxymethyl-pyrimidin-4-yloxy)-benzofuran-3-carboxylic acid methyl ester in 2 ml THF is added and the yellowish solution is stirred for 1¼ h in an oil bath of 110° C. The solution is cooled in an icebath and hydrolyzed with 15 ml of a sat. $NH_4Cl$ solution. After 15 min stirring, the mixture is diluted with EtOAc and water, the aq. phase separated off and extracted twice with EtOAc. The organic layers are washed with water and brine, dried ($Na_2SO_4$) and concentrated. Chromatography (Combi Flash; hexane/EtOAc 4:1→EtOAc) gives the title compound: MS: $[M+1]^+$=520; TLC(hexane/EtOAc 2:1): $R_f$=0.17.

The starting material is prepared as follows:

Step 21.1: 6-(6-benzyloxymethyl-pyrimidin-4-yloxy)-benzofuran-3-carboxylic acid methyl ester 415 mg (3.0 mMol) $K_2CO_3$ and 249 mg (1.5 mMol) KI are added to a solution of 192 mg (1.00 mMol) 6-hydroxy-benzofuran-3-carboxylic acid methyl ester (Step 9.4) and 258 mg (1.1 mMol) 4-benzyloxymethyl-6-chloro-pyrimidine (commercially available; [CAS: 914802-11-2]) in 1.6 ml NMP. This mixture is stirred for 4 h at 100° C., cooled to rt and diluted with water and EtOAc. The aq. phase is separated off and extracted twice with EtOAc. The organic layers are washed with a diluted solution of $Na_2S_2O_3$ and brine, dried ($Na_2SO_4$) and concentrated. Chromatography (Combi Flash; hexane/EtOAc 19:1→1:1) and crystallization from hexane gives the title compound: m.p.: 85-86° C.; MS: $[M+1]^+$=391; TLC(hexane/EtOAc 2:1): $R_f$=0.38.

Example 22

6-(6-Hydroxymethyl-pyrimidin-4-yloxy)-benzofuran-3-carboxylic acid (3-trifluoromethyl-phenyl)-amide

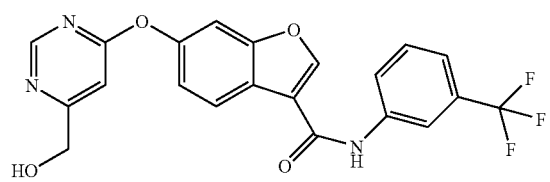

A solution of 133 mg (0.256 mMol) 6-(6-benzyloxymethyl-pyrimidin-4-yloxy)-benzofuran-3-carboxylic acid (3-trifluoromethyl-phenyl)-amide in 13.3 ml $CH_2Cl_2$ is cooled in an icebath. 3.3 ml $H_3CSO_3H$ are added and stirring is continued for 2.5 h at rt. The solution is poured into a vigorousely stirred mixture of 70 g ice and 70 ml sat. $Na_2CO_3$ solution. After 5 min, the mixture is extracted 3 times with EtOAc. The organic layers are washed with water and brine, dried ($Na_2SO_4$) and concentrated. Chromatography (Combi Flash; EtOAc/hexane 1:19→1:1→EtOAc) gives the title compound: m.p.: 181-182° C.; MS: $[M+1]^+$=430; Anal.: C,H, N,F; $^1$H MNR (DMSO-d6): δ ppm 10.56 (s, HN), 8.85 (s, 1H), 8.65 (s, 1H), 8.22 (s, 1H), 8.15 (d, 1H), 8.01 (d, 1H), 7.72 (s, 1H), 7.63 (t, 1H), 7.47 (d, 1H), 7.27 (d, 1H), 7.06 (s, 1H), 5.67 (sb, HO), 4.55 (s, $CH_2$).

Example 23

The following derivatives are obtained analogously to Ex. 21 and Ex. 22.

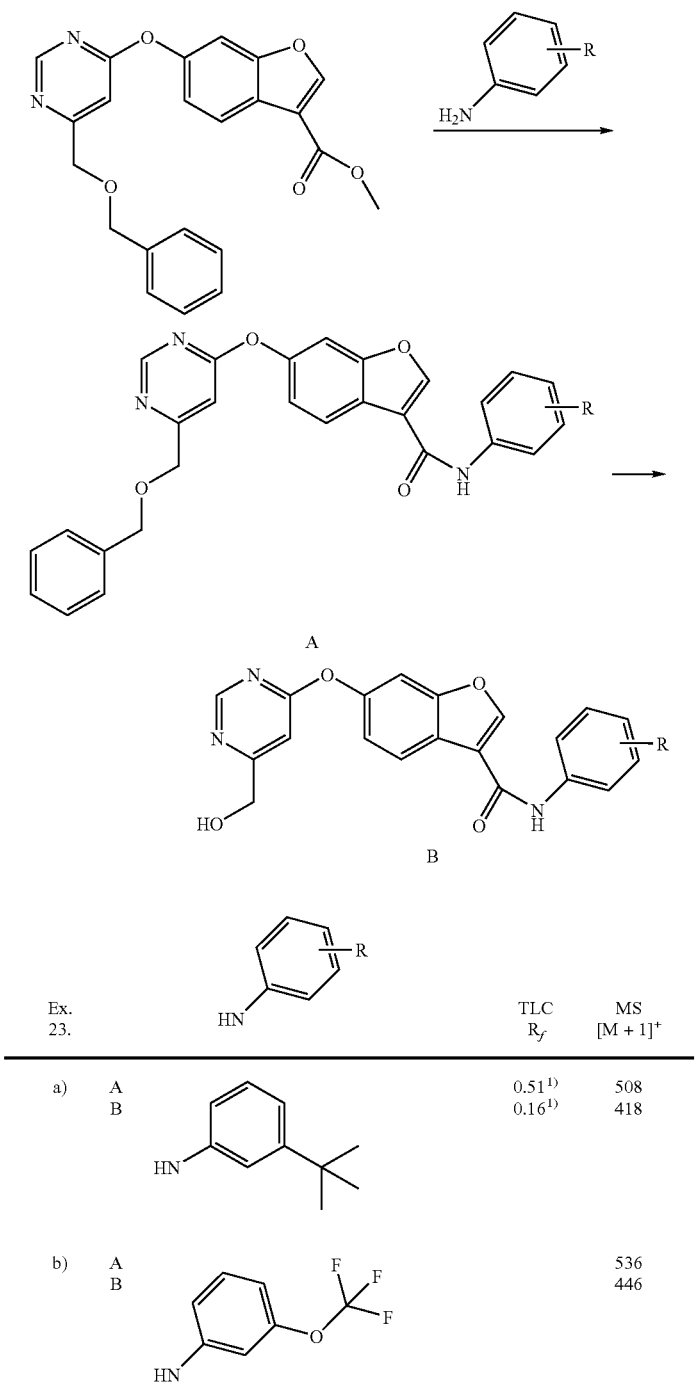

| Ex. 23. | | | TLC $R_f$ | MS $[M+1]^+$ |
|---|---|---|---|---|
| a) | A<br>B | | $0.51^{1)}$<br>$0.16^{1)}$ | 508<br>418 |
| b) | A<br>B | | | 536<br>446 |

| | | | | |
|---|---|---|---|---|
| c) | A<br>B | 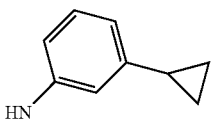 | | 492<br>401 |
| d) | A<br>B | 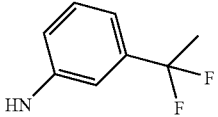 | | 516<br>426 |
| e) | A<br>B | 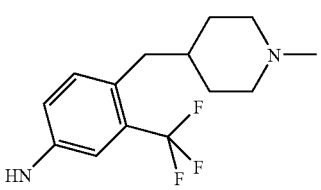 | | |
| f) | A*)<br>B*) | 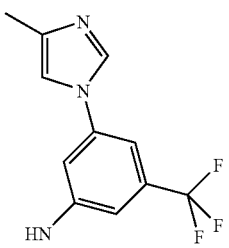 | 0.38[2)]<br>0.13[2)] | 600<br>510 |

[1)]EtOAc/hexane 2:1;
[2)]CH$_2$Cl$_2$/MeOH 9:1;
*)aniline prepared as described in WO 06/135619

Example 24

Dry-Filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 25

Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 liter |
| Tween 80 | 1 liter |

Preparation process: The active ingredient is pulverised and suspended in PEG 400 (polyethylene glycol having an M$_r$ of from approx. 380 to approx. 420, Fluka, Switzerland) and Tween® 80 (polyoxyethylene sorbitan monolaurate, Atlas Chem. Ind. Inc., USA, supplied by Fluka, Switzerland) and ground in a wet pulveriser to a particle size of approx. from 1 to 3 μm. 0.43 g portions of the mixture are then introduced into soft gelatin capsules using a capsule-filling machine.

The invention claimed is:
1. The invention relates to compounds of the formula IB,

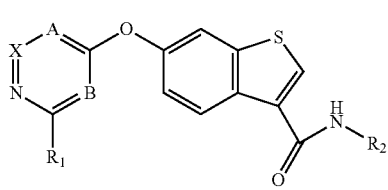

(IB)

wherein
R$_1$ is H; halo; —C$_0$-C$_7$-alkyl-O—R$_3$; —NR$_4$R$_5$;
R$_2$ is substituted aryl;
R$_3$ is H, lower alkyl or phenyl lower alkyl;

R₄ and R₅ are independently selected from the group consisting of H; unsubstituted or substituted lower alkyl; lower alkoxy-carbonyl and amino;

A is N and X and B are both C(R₇), or B is N and X and A are both C(R₇); and

R₇ is selected from the group consisting of H, halo and unsubstituted or substituted lower alkyl;

or a salt thereof.

2. A compound of the formula I according to claim 1, wherein

R₁ is H; chloro, CH₂OH, CH₂OCH₂ phenyl, NH₂, NHNH₂, NHCH₃ or NHCOOCH₃;

R₂ is phenyl substituted by one or two substituents selected from the group consisting of halo C₁₋₇alkyl, trifluoromethoxy, C₁₋₇ alkyl, phenoxy, halogen, C₁₋₇ alkylpiperazinyl C₁₋₇alkyl, C₁₋₇alkyl, C₁₋₇ alkoxy, C₃-C₈-cycloalkyl, C₁₋₇alkylpiperidinyl C₁₋₇alkyl and C₁₋₇alkylimidazolyl;

A is N and X and B are both C(R₇), or B is N and X and A are both C(R₇); and

R₇ is hydrogen;

or a salt thereof.

3. A compound of the formula I according to claim 1, selected from the group consisting of 6-(2-amino-pyrimidin-4-yloxy)-benzo[b]thiophene-3-carboxylic acid (3-trifluoromethyl-phenyl)-amide, 6-(2-amino-pyrimidin-4-yloxy)-benzo[b]thiophene-3-carboxylic acid (4-fluoro-3-trifluoromethyl-phenyl)-amide, 6-(2-amino-pyrimidin-4-yloxy)-benzo[b]thiophene-3-carboxylic acid (3-trifluoromethoxy-phenyl)-amide, 6-(2-amino-pyrimidin-4-yloxy)-benzo[b]thiophene-3-carboxylic acid (3-cyclopropyl-phenyl)-amide, 6-(2-amino-pyrimidin-4-yloxy)-benzo[b]thiophene-3-carboxylic acid (3-isopropyl-phenyl)-amide, 6-(2-amino-pyrimidin-4-yloxy)-benzo[b]thiophene-3-carboxylic acid (4-tert-butyl-phenyl)-amide, 6-(2-amino-pyrimidin-4-yloxy)-benzo[b]thiophene-3-carboxylic acid (3,4-dimethyl-phenyl)-amide, 6-(2-amino-pyrimidin-4-yloxy)-benzo[b]thiophene-3-carboxylic acid (3,5-dimethoxy-phenyl)-amide, 6-(2-amino-pyrimidin-4-yloxy)-benzo[b]thiophene-3-carboxylic acid (4-methyl-3-trifluoromethyl-phenyl)-amide, 6-(2-amino-pyrimidin-4-yloxy)-benzo[b]thiophene-3-carboxylic acid (3-tert-butyl-phenyl)-amide, 6-(2-amino-pyrimidin-4-yloxy)-benzo[b]thiophene-3-carboxylic acid (3-phenoxy-phenyl)-amide, 6-(2-amino-pyrimidin-4-yloxy)-benzo[b]thiophene-3-carboxylic acid [4-(4-methyl-piperazin-1-ylmethyl)-3-trifluoromethyl-phenyl]-amide, (4-{3-[4-(4-methyl-piperazin-1-ylmethyl)-3-trifluoromethyl-phenylcarbamoyl]-benzo[b]thiophene-6-yloxy}-pyrimidin-2-yl)-carbamic acid methyl ester, 6-(2-Hydroxymethyl-pyrimidin-4-yloxy)-benzo[b]thiophene-3-carboxylic acid (3-tert-butyl-phenyl)-amide, 6-(2-Hydroxymethyl-pyrimidin-4-yloxy)-benzo[b]thiophene-3-carboxylic acid (3-trifluoromethyl-phenyl)-amide, 6-(2-Hydroxymethyl-pyrimidin-4-yloxy)-benzo[b]thiophene-3-carboxylic acid (3-trifluoromethoxy-phenyl)-amide, 6-(2-Hydroxymethyl-pyrimidin-4-yloxy)-benzo[b]thiophene-3-carboxylic acid (3-cyclopropyl-phenyl)-amide, 6-(2-Hydroxymethyl-pyrimidin-4-yloxy)-benzo[b]thiophene-3-carboxylic acid (3-isopropyl-phenyl)-amide, 6-(2-Hydroxymethyl-pyrimidin-4-yloxy)-benzo[b]thiophene-3-carboxylic acid [3-(1,1-difluoro-ethyl)-phenyl]-amide, 6-(2-Hydroxymethyl-pyrimidin-4-yloxy)-benzo[b]thiophene-3-carboxylic acid (4-methyl-3-trifluoromethyl-phenyl)-amide, 6-(2-Hydroxymethyl-pyrimidin-4-yloxy)-benzo[b]thiophene-3-carboxylic acid (4-tert-butyl-phenyl)-amide, 6-(2-Hydroxymethyl-pyrimidin-4-yloxy)-benzo[b]thiophene-3-carboxylic acid [4-(1-methyl-piperidin-4-ylmethyl)-3-trifluoromethyl-phenyl]-amide, 6-(6-Hydroxymethyl-pyrimidin-4-yloxy)-benzo[b]thiophene-3-carboxylic acid (4-fluoro-3-trifluoromethyl-phenyl)-amide, 6-(6-Hydroxymethyl-pyrimidin-4-yloxy)-benzo[b]thiophene-3-carboxylic acid (3-trifluoromethyl-phenyl)-amide, 6-(6-Hydroxymethyl-pyrimidin-4-yloxy)-benzo[b]thiophene-3-carboxylic acid (3-trifluoromethoxy-phenyl)-amide, 6-(6-Hydroxymethyl-pyrimidin-4-yloxy)-benzo[b]thiophene-3-carboxylic acid (3-cyclopropyl-phenyl)-amide, 6-(6-Hydroxymethyl-pyrimidin-4-yloxy)-benzo[b]thiophene-3-carboxylic acid (3-tert-butyl-phenyl)-amide, 6-(6-Hydroxymethyl-pyrimidin-4-yloxy)-benzo[b]thiophene-3-carboxylic acid (4-tert-butyl-phenyl)-amide, 6-(6-Hydroxymethyl-pyrimidin-4-yloxy)-benzo[b]thiophene-3-carboxylic acid [4-methyl-3-trifluoromethyl-phenyl]-amide, and 6-(6-Hydroxymethyl-pyrimidin-4-yloxy)-benzo[b]thiophene-3-carboxylic acid [4-(1-methyl-piperidin-4-ylmethyl)-3-trifluoromethyl-phenyl]-amide, or a pharmaceutically acceptable salt thereof.

4. A pharmaceutical preparation comprising a compound of the formula I, or a salt thereof according to claim 1 and at least one pharmaceutically acceptable carrier material.

5. A method of treating ovarian cancer by administering a compound of claim 1, or a pharmaceutically acceptable salt thereof, to a patient in need of such therapy.

* * * * *